United States Patent [19]

Makino et al.

[11] Patent Number: 5,116,405

[45] Date of Patent: May 26, 1992

[54] PYRIDINESULFONAMIDE DERIVATIVES AND HERBICIDES

[75] Inventors: Kenzi Makino; Katsushi Morimoto; Shigeaki Akiyama; Hideaki Suzuki; Takeshi Nagaoka, all of Funabashi; Koichi Suzuki, Shiraoka; Tsutomu Nawamaki, Shiraoka; Shigeomi Watanabe, Shiraoka, all of Japan

[73] Assignee: Nissan Chemical Industries Ltd., Tokyo, Japan

[21] Appl. No.: 606,311

[22] Filed: Oct. 31, 1990

[30] Foreign Application Priority Data

Nov. 6, 1989 [JP] Japan ............... 1-288313
Jun. 11, 1990 [JP] Japan ............... 2-152325
Sep. 11, 1990 [JP] Japan ............... 2-240264

[51] Int. Cl.$^5$ .................. A01N 43/40; C07D 401/12
[52] U.S. Cl. .................................. 71/94; 71/88; 71/91; 71/92; 546/279; 546/256; 546/270; 546/277; 546/167; 546/271; 544/333; 544/215; 544/180; 544/353; 544/356; 544/284
[58] Field of Search .................. 546/279; 71/94

[56] References Cited

U.S. PATENT DOCUMENTS 4,927,452  5/1990  Wellinga et al. ............... 548/374

FOREIGN PATENT DOCUMENTS 0052856  6/1982  European Pat. Off. .
0184385  6/1986  European Pat. Off. .
0269141  6/1988  European Pat. Off. .
0301784  2/1989  European Pat. Off. .
303383   2/1989  European Pat. Off. .

OTHER PUBLICATIONS

Chemical Abstracts, vol. 108, No. 3, Jan. 18, 1988, Columbus, Ohio, U.S.A. Kimura, Fumio et al., "Process for the Preparation of (Triazinyl- and (Pyrimidinylaminocarbonyl) Pyridine-Sulfonamides as Herbicides" p. 607, column 1, abstract No. 21 930s&Jpn.

*Primary Examiner*—Jane T. Fan
*Attorney, Agent, or Firm*—Oblon, Spivak, McClelland, Maier & Neustadt

[57] ABSTRACT

A pyridinesulfonamide derivative of the formula (I) and a salt thereof:

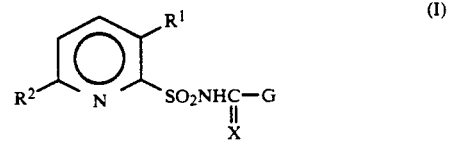

wherein $R^1$ is a halogen atom, a trifluoromethyl group, a $C_1$-$C_6$ alkoxycarbonyl group, a $C_1$-$C_6$ mono- or di-alkylaminocarbonyl group, a $C_1$-$C_6$ alkxoy group, a $C_1$-$C_6$ alkylsulfonyl group, a $C_1$-$C_6$ alkylthio group, a $C_1$-$C_6$ alkyl group substituted by a $C_1$-$C_6$ alkoxy group, a $C_1$-$C_6$ alkyl group substituted by a $C_1$-$C_6$ mono- or poly-halogenoalkoxy group, a $C_1$-$C_6$ mono- or poly-halogenoalkoxy group, a $C_1$-$C_6$ mono- or di-alkylaminosulfonyl group, a $C_1$-$C_6$ alkoxyaminosulfonyl group substituted by a $C_1$-$C_6$ alkyl group, a nitro group, a $C_1$-$C_6$ alkyl group substituted by a $C_1$-$C_6$ alkylthio group, a $C_1$-$C_5$ alkyl group substituted by a $C_1$-$C_6$ alkylsulfonyl group, or a $C_1$-$C_6$ alkyl group substituted by a $C_1$-$C_6$ alkoxycarbonyl group;

$R^2$ is a hydrogen atom or a halogen atom;

X is a oxygen atom or a sulfur atoms; and

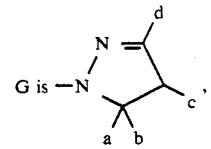

which are useful as herbicides.

24 Claims, No Drawings

PYRIDINESULFONAMIDE DERIVATIVES AND HERBICIDES

The present invention relates to novel pyridinesulfonamide derivatives and salts thereof, and herbicides containing such compounds as active ingredients.

It is indispensable to use herbicides to protect important crop plants such as rice, wheat, corn, soybean, cotton and sugar beet from weeds and thereby to increase the harvest. Especially in recent years, a selective herbicide is desired which is capable of selectively killing weeds without showing any phytotoxicity against crop plants when applied to the foliages of crop plants and weeds simultaneously in a field where such useful crop plants and weeds are coexistent. Further, with a view to avoiding environmental pollution and reducing the costs for transportation and application, researches and developments have been conducted for many years for compounds having high herbicidal effects at low doses. Some of the compounds having such properties are presently used as selective herbicides. However, there still exists a need for new compounds having such properties.

As the prior art showing a chemical structure similar to that of the compounds of the present invention, Japanese Unexamined Patent Publication No. 267576/1986 discloses pyridinesulfonylurea compounds, and Japanese Unexamined Patent Publication No. 122671/1988 discloses sufonamide compounds having a pyrazoline structure.

In Japanese Unexamined Patent Publication No. 122671/1988, heteroarylsulfonamide compounds are generally and broadly claimed on the basis of the disclosure of pyrazolesulfonamide derivatives and thiophenesulfonamide derivatives in addition to substituted benzene sulfonamide derivatives and substituted benzylsulfonamide derivatives, as sulfonamide compounds having a pyrazoline structure. However, in this publication, the compounds of the present invention are not specifically disclosed, and no specific description is given also as to the herbicidal activities of pyrazolesulfonamide derivatives although the usefulness of the heteroarylsulfonamide compounds are generally described.

Pyridinesulfonamide derivatives having a pyrazoline structure, like the compounds of the present invention, have not been known at all, and they are novel compounds.

The present inventors have conducted extensive researches over years to develop selective herbicides for important crop plants and have studied herbicidal properties of many compounds with an aim to find out compounds having higher herbicidal activities as well as selectivity. As a result, it has been found that pyridinesulfonamide derivatives of the following formula (I) and agriculturally suitable salts thereof (hereinafter referred to as the compounds of the present invention) exhibit remarkably strong herbicidal activities against many weeds in soil treatment or in foliage treatment and at the same time have a high level of safety for important crop plants such as wheat, corn, cotton, soybean, sugar beet and rice. The present invention has been accomplished on the basis of this discovery. On the other hand, since the compounds of the present invention show high herbicidal activities at a very low dose as compared with conventional herbicides, they are also useful as herbicides for orchards or for non-agricultural fields.

Namely, the present invention provides a pyridinesulfonamide derivative of the formula (I) and a salt thereof:

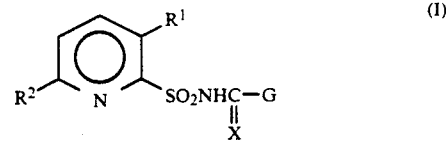

wherein $R^1$ is a halogen atom, a trifluoromethyl group, a $C_1$-$C_6$ alkoxycarbonyl group, a $C_1$-$C_6$ mono- or dialkylaminocarbonyl group, a $C_1$-$C_6$ alkoxy group alkylsulfonyl group, a $C_1$-$C_6$ alkylthio group, a $C_1$-$C_6$ alkyl group substituted by a $C_1$-$C_6$ alkoxy group, a $C_1$-$C_6$ alkyl group substituted by a $C_1$-$C_6$ mono- or polyhalogenoalkoxy group, a $C_1$-$C_6$ mono- or polyhalogenoalkoxy group, a $C_1$-$C_6$ mono- or dialkylaminosulfonyl group, a $C_1$-$C_6$ alkoxyaminosulfonyl group substituted by a $C_1$-$C_6$ alkyl group, a nitro group, a $C_1$-$C_6$ alkyl group substituted by a $C_1$-$C_6$ alkylthio group, a $C_1$-$C_6$ alkyl group Substituted by a $C_1$-$C_6$ alkylsulfonyl group, or a $C_1$-$C_6$ alkyl group substituted by a $C_1$-$C_6$ alkoxycarbonyl group;

$R^2$ is a hydrogen atom or a halogen atom;

X is a oxygen atom or a sulfur atom; and

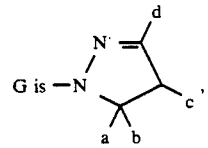

wherein each of a, b, c and d independently represents a hydrogen atom, a $C_1$-$C_6$ alkyl group, a $C_2$-$C_6$ alkenyl group, a $C_2$-$C_6$ alkynyl group, a $C_1$-$C_6$ alkyl group mono- or poly substituted by a halogen atom, a $C_1$-group, a $C_1$-$C_6$ alkyl group substituted by a $C_1$-$C_6$ alkoxy group, a $C_1$-$C_6$ alkoxycarbonyl group, a $C_1$-$C_6$ alkyl group substituted by a $C_1$-$C_6$ alkylthio group, a $C_1$-$C_6$ alkyl group Substituted by a $C_1$-$C_6$ alkylsulfonyl group, a $C_1$-$C_6$ alkylthio group, a $C_1$-$C_6$ alkylcarbonyl group, a $C_3$-$C_7$ cycloalkyl group, a $C_3$-$C_7$ cycloalkenyl group, a cyano group, a phenyl or benzyl group (provided that this phenyl or benzyl group may be mono- or poly-substituted by a halogen atom, a trifluoromethyl group, a $C_1$-$C_6$ alkyl group, a $C_1$-$C_6$ alkoxy group, a $C_1$-$C_6$ alkoxycarbonyl group or a nitro group), a 5- or 6-membered heterocyclic group (provided that such a heterocyclic group contains from 1 to 3 hetero atoms selected from the group consisting of nitrogen atoms, oxygen atoms and sulfur atoms in the ring, or contains a sulfonyl group, and such a heterocyclic group may be mono- or poly-substituted by a $C_1$-$C_6$ alkyl group, a $C_1$-$C_6$ alkoxy group, a halogen atom, a trifluoromethyl group, a nitro group or a $C_1$-$C_6$ alkoxycarbonyl group), a naphthyl group, a benzene-condensed heterocyclic group (provided that such a benzene-condensed heterocyclic group contains 1 or 2 hetero atoms selected from the group consisting of nitrogen atoms, oxygen atoms and sulfur atoms in the ring, and such a benzene-condensed heterocyclic group may mono- or poly-substituted by a $C_1$-$C_6$ alkyl group, a $C_1$-$C_6$ alkoxy group, a halogen atom, a trifluoromethyl group, a nitro group or a $C_1$-$C_6$ alkoxycarbonyl group).

The present invention also provides a selective herbicide containing one or more compounds of the present invention as active ingredients.

Now, the present invention will be described in detail with reference to the preferred embodiments.

The compounds of the formula (I) of the present invention can easily be prepared by any one of the following reaction schemes 1 to 3.

Reaction scheme 1

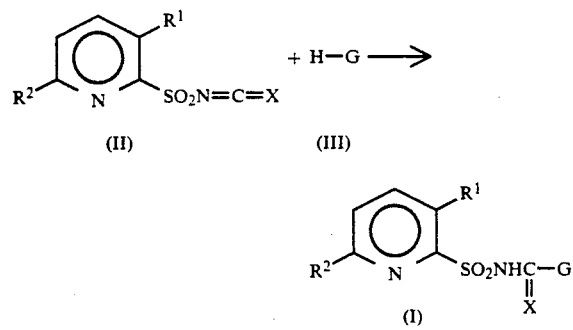

In the above formulas, $R^1$, $R^2$, G and X are as defined above.

Namely, a pyridinesulfonyliso(thio)cyanate derivative (II) is dissolved in a sufficiently dried inert solvent such as benzene, toluene, dichloromethane, dichloroethane, tetrahydrofuran, dioxane, acetonitrile, acetone or methyl ethyl ketone, then a pyrazoline derivative of the formula (III) is added thereto, and the mixture is stirred, whereby the reaction usually proceeds swiftly and the compound (I) of the present invention is obtained. When the reaction hardly proceeds, a very small amount of a suitable base such as triethylamine, triethylenediamine, pyridine, 1,8-diazabicyclo[5,4,0]-7-undecene (DBU), a sodium alkoxide, sodium hydride or potassium carbonate may be added, whereby the reaction readily proceeds.

Reaction scheme 2

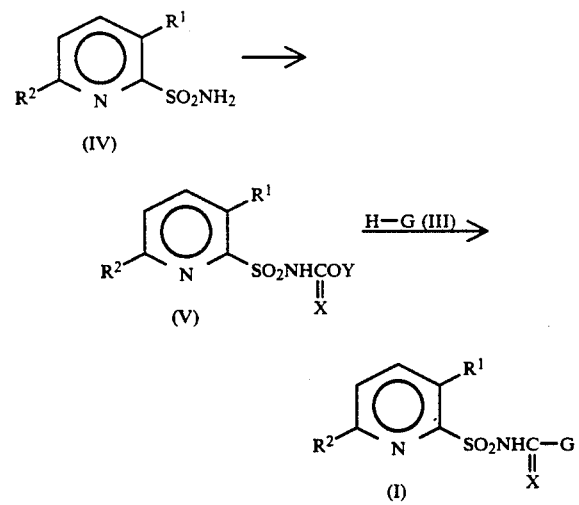

In the above formulas, $R^1$, $R^2$, G and X are as defined above, and Y is a $C_1$-$C_6$ alkyl group or a phenyl group.

Namely, a pyridinesulfonamide derivative (IV) is reacted with chloro(thio)formic acid ester or (thio)carbonic acid diester in a solvent such as acetone, methyl ethyl ketone, acetonitrile, tetrahydrofuran, dioxane, dichloromethane, dichloroethane, N,N-dimethylformamide, benzene or toluene in the presence of a base such as pyridine, triethylamine, 1,8-diazabicyclo[5,4,0]-7-undecene (DBU), potassium carbonate, a sodium alkoxide, sodium hydride, sodium hydroxide or potassium hydroxide to obtain a compound (V). Then, it is heated together with a compound (III) in a solvent such as tetrahydrofuran, dioxane, benzene, toluene, acetone, methyl ethyl ketone, dichloromethane, dichloroethane or N,N-dimethylformamide in the presence of a base such as pyridine, triethylamine, DBU, potassium carbonate, a sodium alkoxide, sodium hydride, sodium hydroxide or potassium hydroxide to obtain the compound (I) of the present invention.

Reaction scheme 3

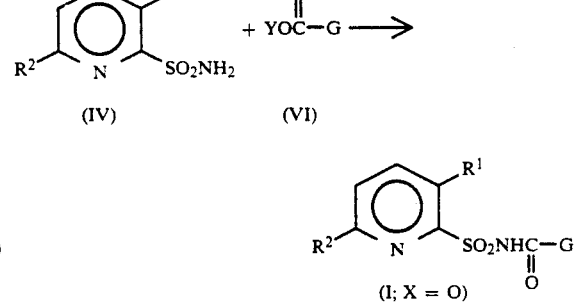

In the above formulas, $R^1$, $R^2$, G and Y are as defined above.

Namely, a pyridinesulfonamide derivative (IV) is reacted with a carbamate derivative (VI) in a solvent such as acetone, methyl ethyl ketone, acetonitrile, tetrahydrofuran, dioxane, dichloromethane, dichloroethane, N,N-dimethylformamide, benzene or toluene in the presence of an inorganic base such as potassium carbonate, sodium hydroxide or potassium hydroxide, or an organic base such as triethylamine, pyridine or DBU, to obtain the compound of the present invention (I; X=O).

The pyridinesulfonyliso(thio)cyanate derivative (II) to be used as a starting material in reaction scheme 1 can be synthesized from a pyridinesulfonamide derivative (IV) in accordance with the methods disclosed in e.g. Japanese Unexamined Patent Publications No. 148879/1983, No. 31775/1984 and No. 13266/1980.

The pyridinesulfonamide derivative (IV) to be used as a starting material in reaction schemes 2 and 3 can be synthesized in accordance with the methods disclosed in e.g. Japanese Unexamined Patent Publications No. 223180/1987 and No. 267576/1986.

The pyrazoline (III) to be used as a starting material for the above reactions, can readily be synthesized in accordance with e.g. Japanese Unexamined Patent Publication No. 122671/1988. Representative examples are shown as reaction schemes 4 and 5.

Reaction scheme 4

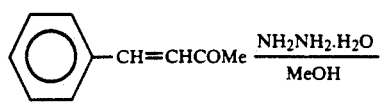

Reaction scheme 4

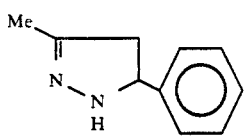

Reaction scheme 5

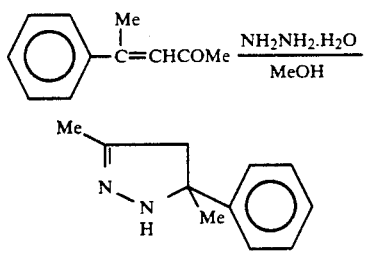

Now, the syntheses of the compounds of the present invention will be described in detail with reference to Reference Example and Preparation Example. However, it should be understood that the present invention is by no means restricted by such specific Examples.

REFERENCE EXAMPLE

Preparation of methyl N-)3-trifluoromethylpyridine-2-sulfonyl)carbamate

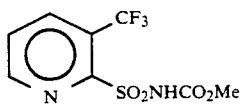

Methyl chloroformate (3.31 g, 35 mmol) was added under cooling with ice to a dry acetonitrile (150 ml) solution containing 3-trifluoromethylpyridine-2-sulfonamide (7.91 g, 35 mmol) and triethylamine (16 ml), and the mixture was continuously stirred at room temperature for 3 hours. Then, the solvent was distilled off under reduced pressure, and the residue was dissolved in 300 ml of water. A small amount of insoluble substances were removed by filtration, and the filtrate was adjusted to pH of 1 to 2 with concentrated hydrochloric acid under cooling with ice. Precipitated crystals were collected by filtration and thoroughly washed with water, then washed with a solvent mixture of ethyl ether/n-hexane and dried to obtain 4.4 g of desired methyl N-(3-trifluoromethylpyridine-2-sulfonyl)carbamate. Melting point: 128°–129° C.

PREPARATION EXAMPLE 1

Preparation of 1-(3-trifluoromethylpyridine-2-sulfonylcarbamoyl)-3-methyl-5-phenyl-2-pyrazoline

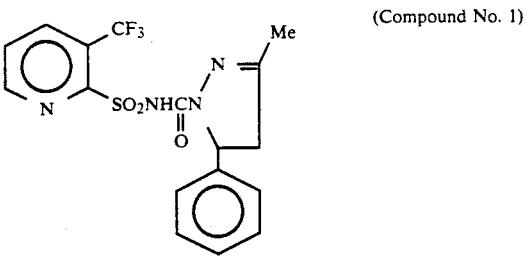

(Compound No. 1)

A dry dioxane (10 ml) solution containing methyl N-(3-trifluoromethylpyridine-2-sulfonyl)carbamate (0.43 g, 1.5 mmol), 3-methyl-5-phenyl-2-pyrazoline (0.48 g, 3.0 mmol) and pyridine (0.45 g) gas refluxed under heating and stirring for one hour. After cooling the mixture, the solvent was distilled off under reduced pressure, and the residue was stirred together with ethyl ether. Precipitated crystals were collected by filtration and then thoroughly washed with ethyl ether, and the crystals were suspended in 20 ml of water. Then, the pH was adjusted to a level of from 1 to 2 with concentrated hydrochloric acid, and the suspension was stirred at room temperature for 5 minutes. Crystals were collected by filtration, thoroughly washed with water and then with ethyl ether and dried to obtain 0.51 g of desired 1-(3-trifluoromethylpyridine-2-sulfonylcarbamoyl)-3-methyl-5-phenyl-2-pyrazoline. Melting point: 185°–187° C.

PREPARATION EXAMPLE 2

Preparation of 1-(3-trifluoromethylpyridine-2-sulfonylcarbamoyl)-3,5-dimethyl-5-phenyl-2-pyrazoline

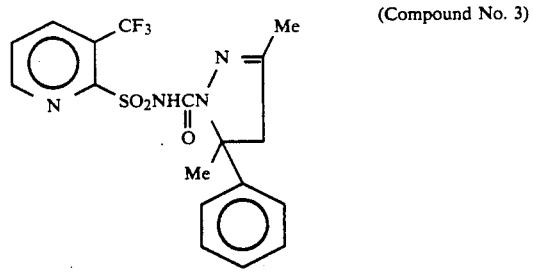

(Compound No. 3)

A dry dioxane (10 ml) solution containing methyl N-(3-trifluoromethylpyridine-2-sulfonyl)carbamate (0.43 g, 1.5 mmol), 3,5-dimethyl-5-phenyl-2-pyrazoline (0.52 g, 3.0 mmol) and pyridine (0.45 g) was refluxed under heating and stirring for one hour. After cooling the mixture, the solvent was distilled off under reduced pressure, and the residue was stirred together with ethyl ether. Precipitated crystals were collected by filtration and then thoroughly washed with ethyl ether, and the crystals were suspended in 20 ml of water. Then, the pH was adjusted to a level of from 1 to 2 with concentrated hydrochloric acid, and the suspension was stirred at room temperature for 5 minutes. Crystals were collected by filtration, thoroughly washed with water and then with ethyl ether and dried to obtain 0.55 g of sired 1-(3-trifluoromethylpyridine-2-sulfonylcarbamoyl)-3,5-dimethyl-5-phenyl-2-pyrazoline. Melting point: 152°–153° C.

The structures and the physical values or properties of the compounds prepared in the same manner as the above Preparation Example are shown below.

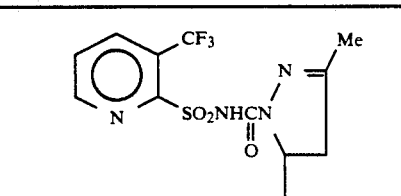

Compound No. 1     m.p. 185–187° C.

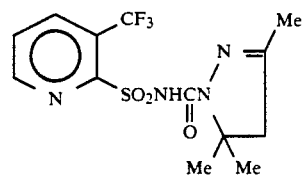

Compound No. 2     m.p. 183–184° C.

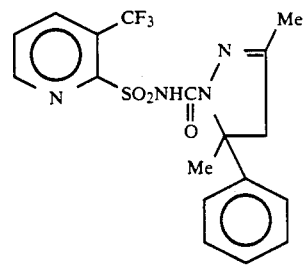

Compound No. 3     m.p. 152–153° C.

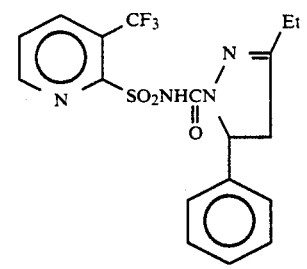

Compound No. 4     m.p. 160–161° C.

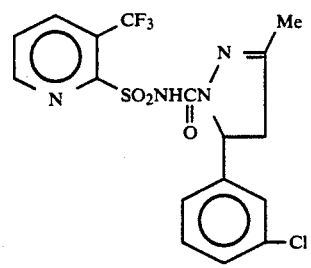

Compound No. 5     m.p. 177–178° C.

-continued

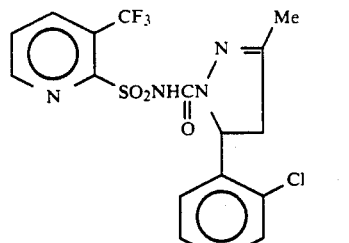

Compound No. 6     m.p. 144–145° C.

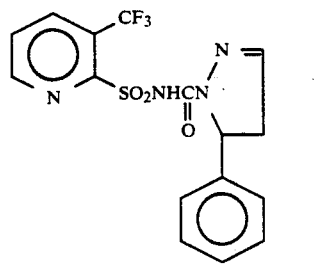

Compound No. 7     m.p. 138–140° C.

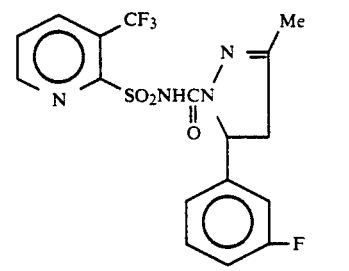

Compound No. 8     m.p. 185–186° C.

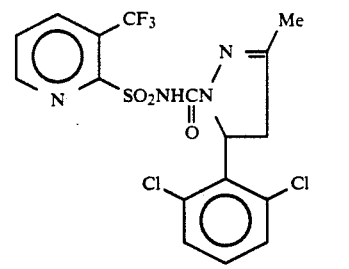

Compound No. 9     m.p. 195–196° C.

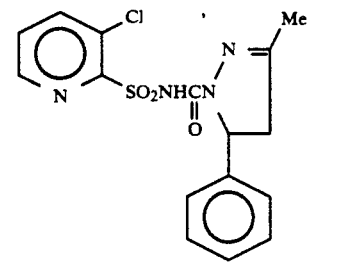

Compound No. 10     m.p. 157–158° C.

-continued
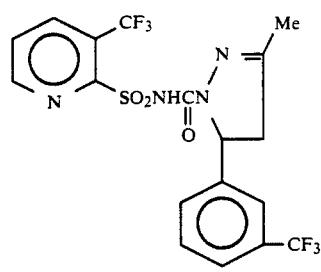
Compound No. 11   m.p. 150~151° C.
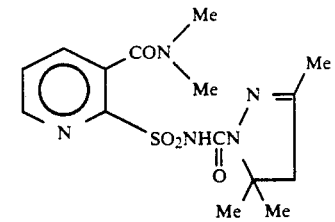
Compound No. 16   m.p. 207~208° C.
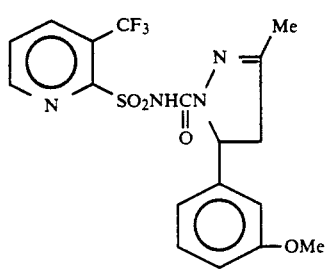
Compound No. 12   m.p. 129~130° C.
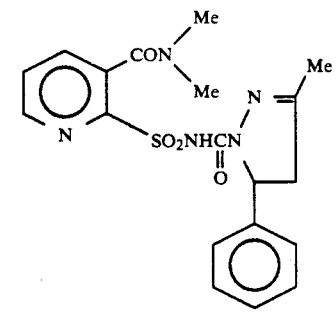
Compound No. 17   Glassy
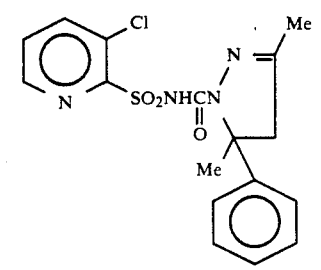
Compound No. 13   m.p. 178~179° C.
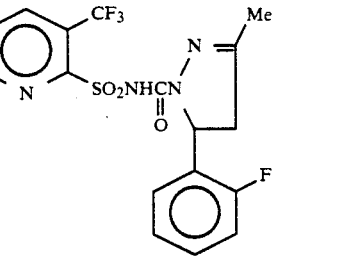
Compound No. 18   m.p. 168~170° C.
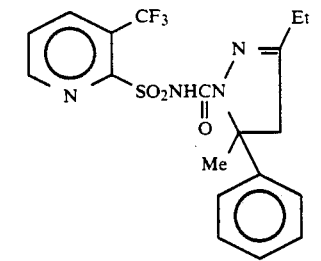
Compound No. 14   Oil
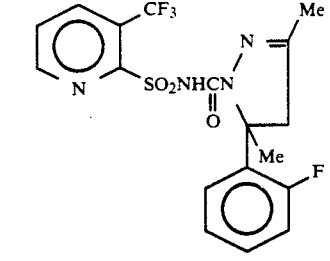
Compound No. 19   m.p. 168~169° C.
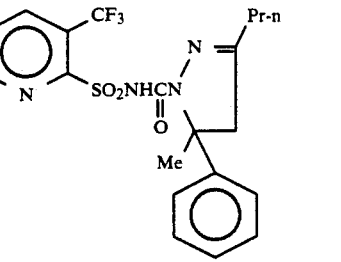
Compound No. 15   m.p. 149~150° C.
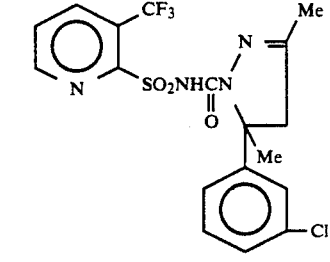
Compound No. 20   m.p. 116~117° C.

-continued
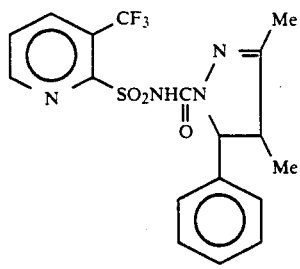
Compound No. 21  m.p. 178.5~179.5° C.
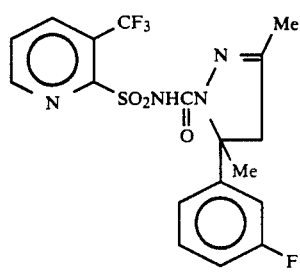
Compound No. 22  m.p. 136~137° C.
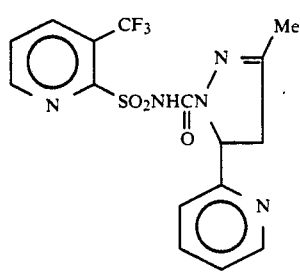
Compound No. 23  m.p. 177~178° C.
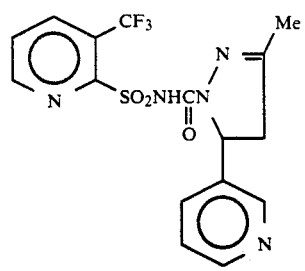
Compound No. 24  m.p. 186~187° C.
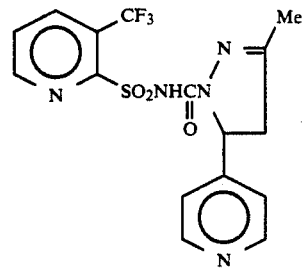
Compound No. 25  m.p. 188~189° C.
-continued
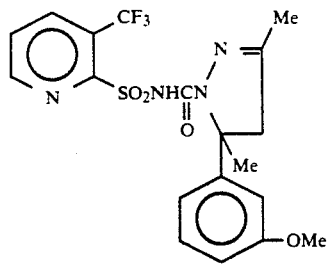
Compound No. 26  m.p. 106~107° C.
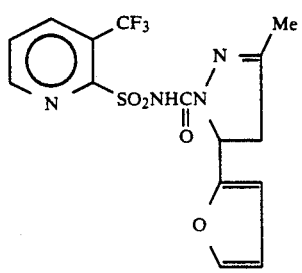
Compound No. 27  m.p. 136~137° C.
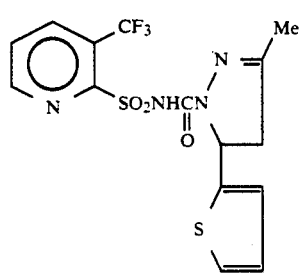
Compound No. 28  m.p. 124~125° C.
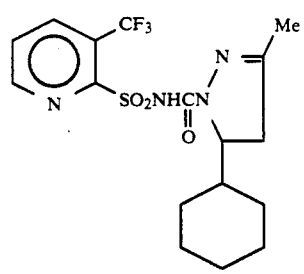
Compound No. 29  m.p. 160~161° C.
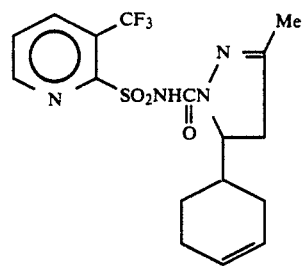
Compound No. 30  m.p. 113~114° C.

-continued

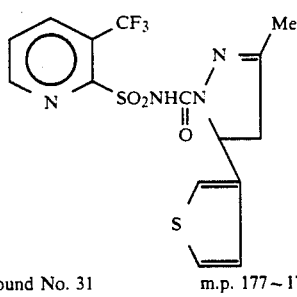

Compound No. 31  m.p. 177~178° C.

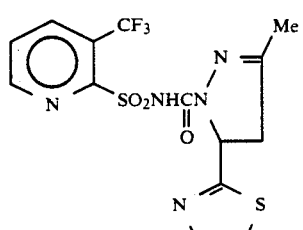

Compound No. 32  m.p. 187~188° C.

Now, Table 1 presents examples of specific compounds of the present invention including the compounds prepared in the preceding Examples. However, it should be understood that the compounds of the present invention are not limited to such specific examples.

In Table 1, Gn in the structural formula has the same meaning as G and includes all of G1 to G479 as defined hereinafter, and the symbols used in the Table have the following meanings: Me: methyl group, Et: ethyl group, Pr-n: n-propyl group, Pr-i: isopropyl group, Bu-n: n-butyl group, Pen-n: n-pentyl group and Ph: phenyl group.

TABLE 1

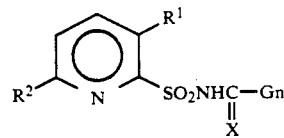

| $R^1$ | $R^2$ | X |
|---|---|---|
| Cl | H | O |
| Cl | H | S |
| Cl | F | O |
| Cl | F | S |
| Cl | Cl | O |
| Cl | Cl | S |
| Br | H | O |
| Br | H | S |
| Br | F | O |
| Br | F | S |
| Br | Cl | O |
| Br | Cl | S |
| $CF_3$ | H | O |
| $CF_3$ | H | S |
| $CF_3$ | F | O |
| $CF_3$ | F | S |
| $CF_3$ | Cl | O |
| $CF_3$ | Cl | S |
| $CO_2Me$ | H | O |
| $CO_2Me$ | H | S |
| $CO_2Me$ | F | O |
| $CO_2Me$ | F | S |
| $CO_2Me$ | Cl | O |
| $CO_2Me$ | Cl | S |
| $CO_2Et$ | H | O |
| $CO_2Et$ | H | S |

TABLE 1-continued

| $R^1$ | $R^2$ | X |
|---|---|---|
| $CO_2Et$ | F | O |
| $CO_2Et$ | F | S |
| $CO_2Et$ | Cl | O |
| $CO_2Et$ | Cl | S |
| $CO_2Pr-n$ | H | O |
| $CO_2Pr-n$ | H | S |
| $CO_2Pr-n$ | F | O |
| $CO_2Pr-n$ | F | S |
| $CO_2Pr-n$ | Cl | O |
| $CO_2Pr-n$ | Cl | S |
| $CONMe_2$ | H | O |
| $CONMe_2$ | H | S |
| $CONMe_2$ | F | O |
| $CONMe_2$ | F | S |
| $CONMe_2$ | Cl | O |
| $CONMe_2$ | Cl | S |
| OMe | H | O |
| OMe | H | S |
| OMe | F | O |
| OMe | F | S |
| OMe | Cl | O |
| OMe | Cl | S |
| OEt | H | O |
| OEt | H | S |
| OEt | F | O |
| OEt | F | S |
| OEt | Cl | O |
| OEt | Cl | S |
| $SO_2Me$ | H | O |
| $SO_2Me$ | H | S |
| $SO_2Me$ | F | O |
| $SO_2Me$ | F | S |
| $SO_2Me$ | Cl | O |
| $SO_2Me$ | Cl | S |
| $SO_2Et$ | H | O |
| $SO_2Et$ | H | S |
| $SO_2Et$ | F | O |
| $SO_2Et$ | F | S |
| $SO_2Et$ | Cl | O |
| $SO_2Et$ | Cl | S |
| SMe | H | O |
| SMe | H | S |
| SMe | F | O |
| SMe | F | S |
| SMe | Cl | O |
| SMe | Cl | S |
| $CH_2OMe$ | H | O |
| $CH_2OMe$ | H | S |
| $CH_2OMe$ | F | O |
| $CH_2OMe$ | F | S |
| $CH_2OMe$ | Cl | O |
| $CH_2OMe$ | Cl | S |
| $CH_2OEt$ | H | O |
| $CH_2OEt$ | H | S |
| $CH_2OEt$ | F | O |
| $CH_2OEt$ | F | S |
| $CH_2OEt$ | Cl | O |
| $CH_2OEt$ | Cl | S |
| $CH_2OCHF_2$ | H | O |
| $CH_2OCHF_2$ | H | S |
| $CH_2OCHF_2$ | F | O |
| $CH_2OCHF_2$ | F | S |
| $CH_2OCHF_2$ | Cl | O |
| $CH_2OCHF_2$ | Cl | S |
| $CH_2OCH_2CF_3$ | H | O |
| $CH_2OCH_2CF_3$ | H | S |
| $CH_2OCH_2CF_3$ | F | O |
| $CH_2OCH_2CF_3$ | F | S |
| $CH_2OCH_2CF_3$ | Cl | O |
| $CH_2OCH_2CF_3$ | Cl | S |
| $OCH_2CH_2Cl$ | H | O |
| $OCH_2CH_2Cl$ | H | S |
| $OCH_2CH_2Cl$ | F | O |

TABLE 1-continued

![structure: pyridine with R1 at 3-position, R2 at 6-position, and SO2NHC(=X)-Gn at 2-position]

| R¹ | R² | X |
|---|---|---|
| OCH₂CH₂Cl | F | S |
| OCH₂CH₂Cl | Cl | O |
| OCH₂CH₂Cl | Cl | S |
| SO₂NMe₂ | H | O |
| SO₂NMe₂ | H | S |
| SO₂NMe₂ | F | O |
| SO₂NMe₂ | F | S |
| SO₂NMe₂ | Cl | O |
| SO₂NMe₂ | Cl | S |
| SO₂N(OMe)Me | H | O |
| SO₂N(OMe)Me | H | S |
| SO₂N(OMe)Me | F | O |
| SO₂N(OMe)Me | F | S |
| SO₂N(OMe)Me | Cl | O |
| SO₂N(OMe)Me | Cl | S |
| NO₂ | H | O |
| NO₂ | H | S |
| NO₂ | F | O |
| NO₂ | F | S |
| NO₂ | Cl | O |
| NO₂ | Cl | S |
| CH₂SMe | H | O |
| CH₂SMe | H | S |
| CH₂SMe | F | O |
| CH₂SMe | F | S |
| CH₂SMe | Cl | O |
| CH₂SMe | Cl | S |
| CH₂SEt | H | O |
| CH₂SEt | H | S |
| CH₂SEt | F | O |
| CH₂SEt | F | S |
| CH₂SEt | Cl | O |
| CH₂SEt | Cl | S |
| CH₂SO₂Me | H | O |
| CH₂SO₂Me | H | S |
| CH₂SO₂Me | F | O |
| CH₂SO₂Me | F | S |
| CH₂SO₂Me | Cl | O |
| CH₂SO₂Me | Cl | S |
| CH₂SO₂Et | H | O |
| CH₂SO₂Et | H | S |
| CH₂SO₂Et | F | O |
| CH₂SO₂Et | F | S |
| CH₂SO₂Et | Cl | O |
| CH₂SO₂Et | Cl | S |
| CH₂CO₂Me | H | O |
| CH₂CO₂Me | H | S |
| CH₂CO₂Me | F | O |
| CH₂CO₂Me | F | S |
| CH₂CO₂Me | Cl | O |
| CH₂CO₂Me | Cl | S |
| CH₂CO₂Et | H | O |
| CH₂CO₂Et | H | S |
| CH₂CO₂Et | F | O |
| CH₂CO₂Et | F | S |
| CH₂CO₂Et | Cl | O |
| CH₂CO₂Et | Cl | S |

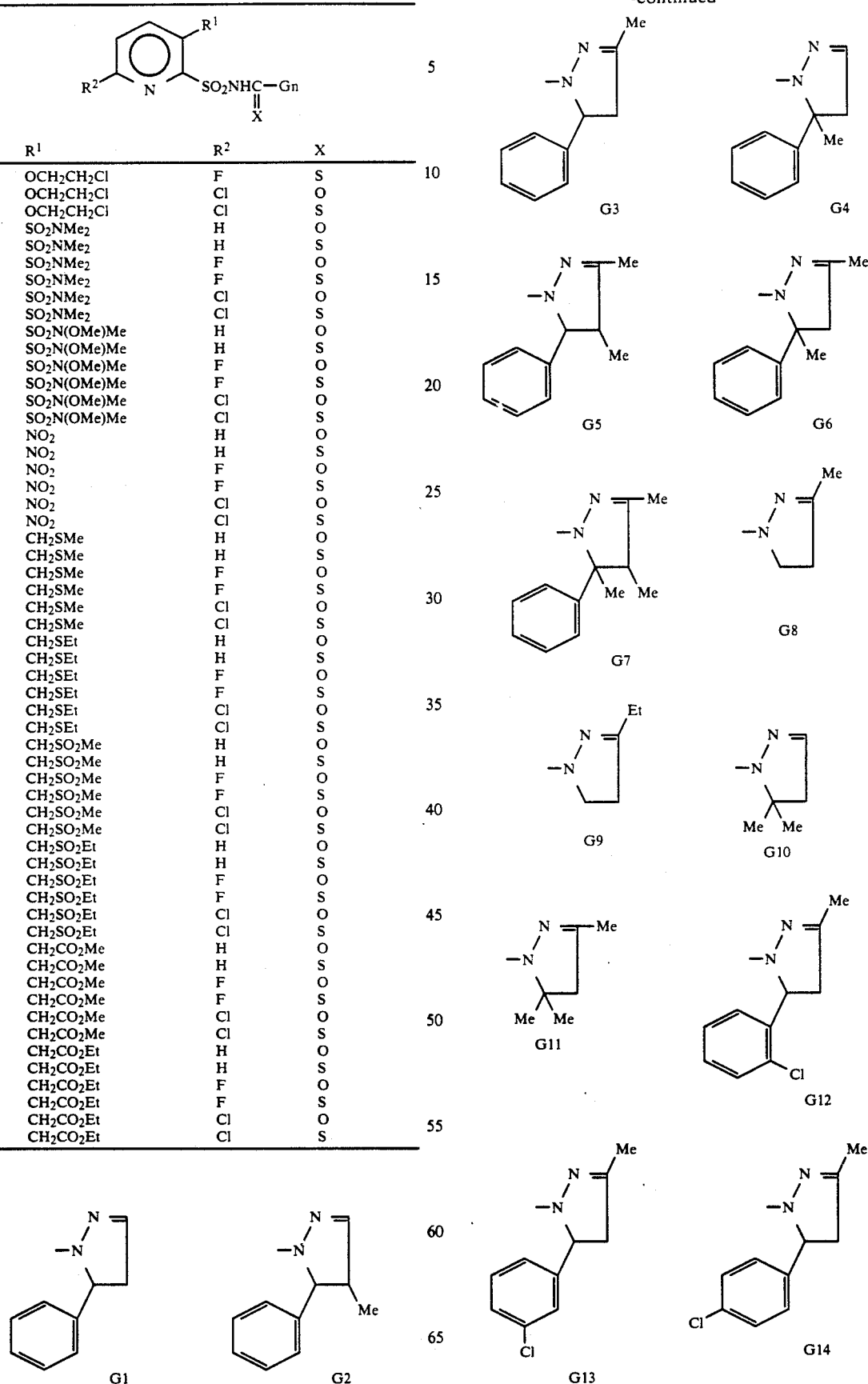

-continued

-continued
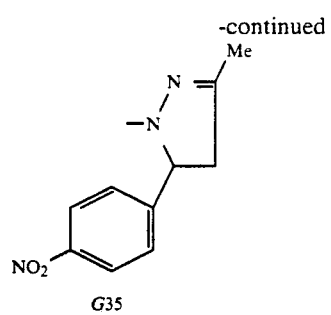
G35
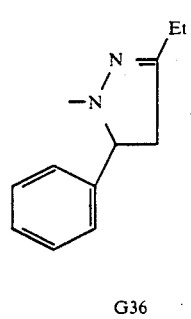
G36
-continued
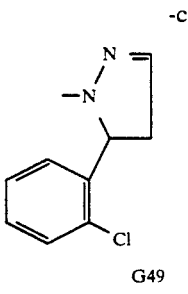
G49
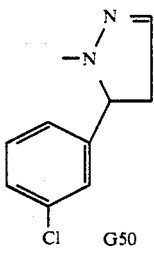
G50
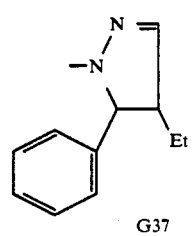
G37
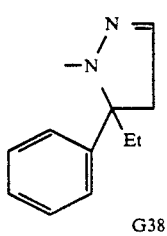
G38
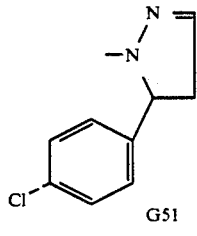
G51
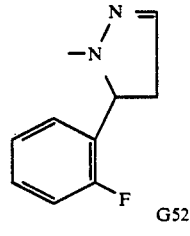
G52
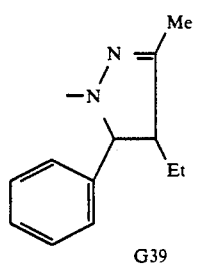
G39
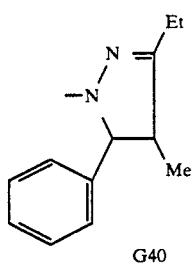
G40
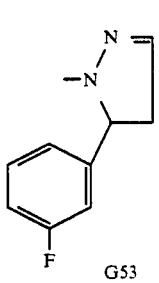
G53
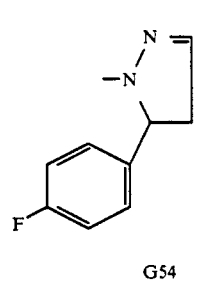
G54
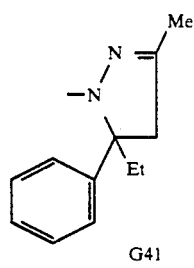
G41
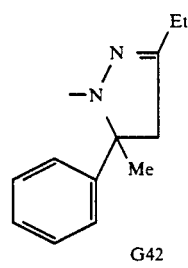
G42
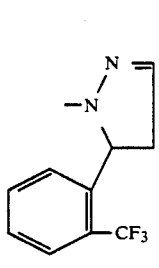
G55
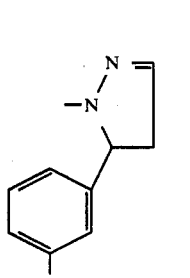
G56
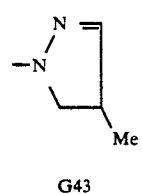
G43
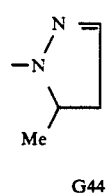
G44
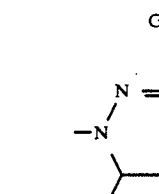
G57
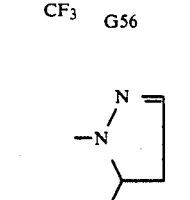
G58
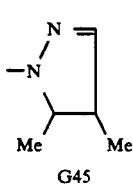
G45
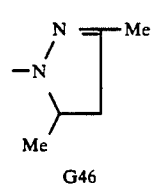
G46
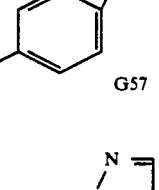
G59
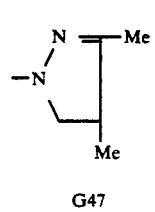
G47
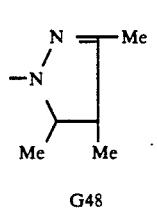
G48
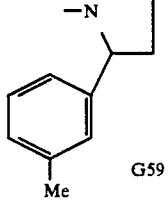
G60

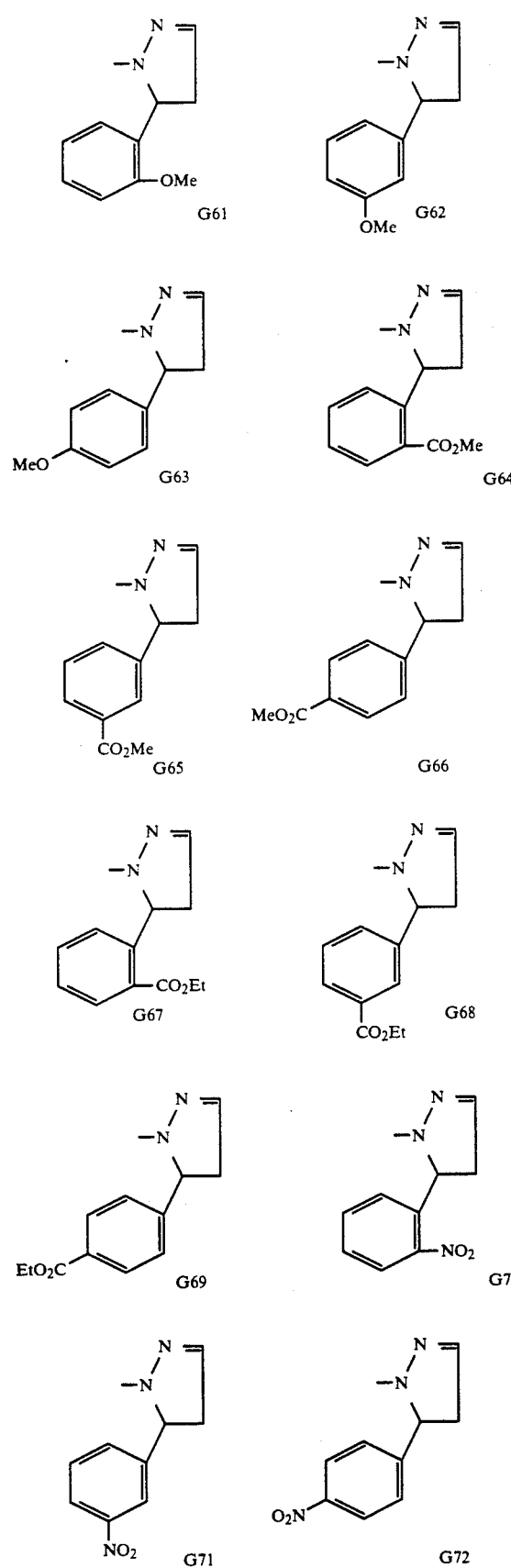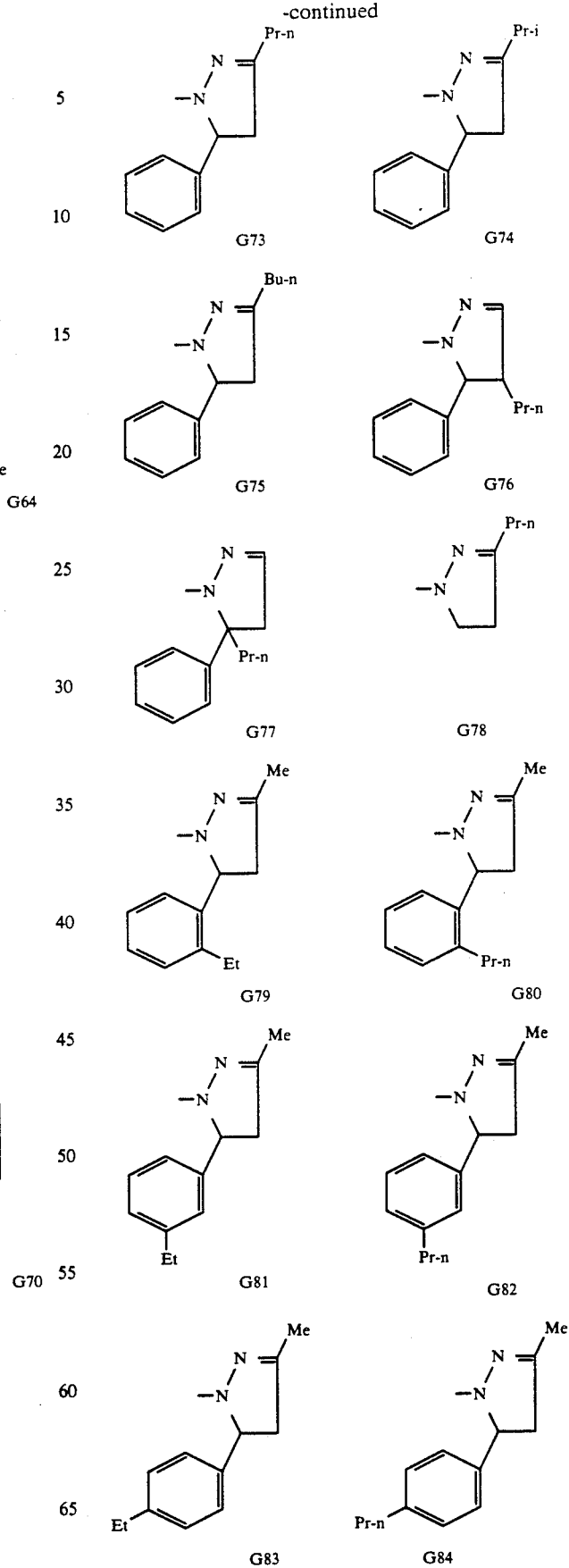

-continued
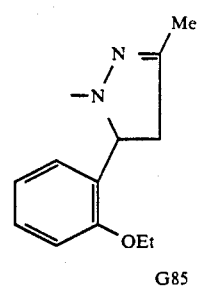
G85
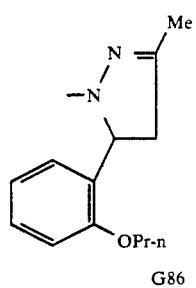
G86
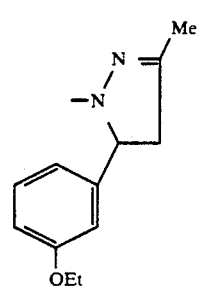
G87
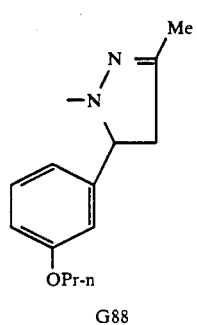
G88
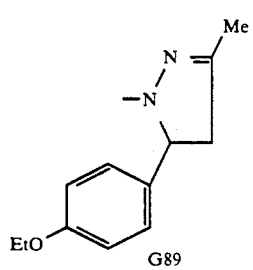
G89
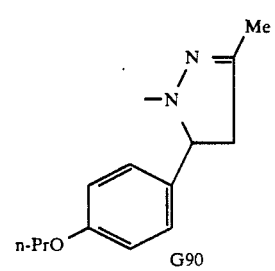
G90
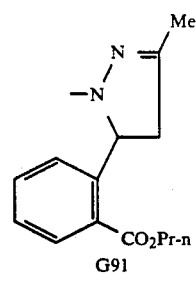
G91
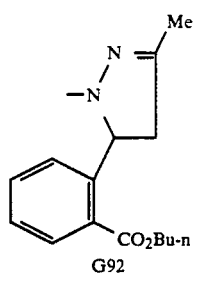
G92
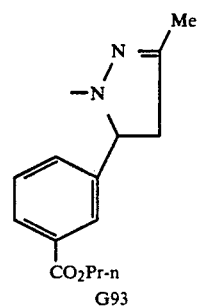
G93
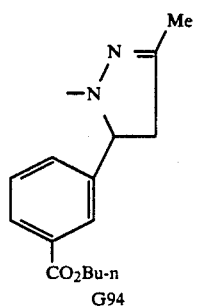
G94
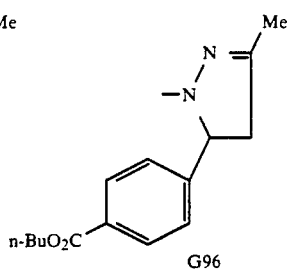
G95
G96
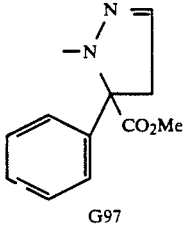
G97
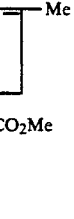
G98
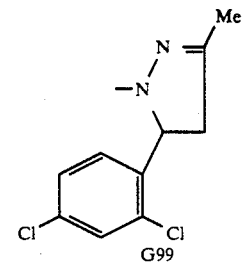
G99
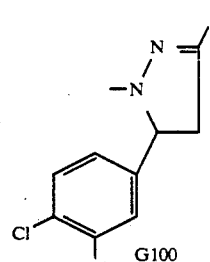
G100
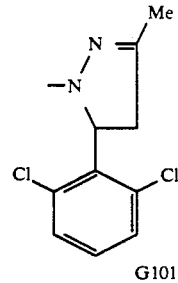
G101
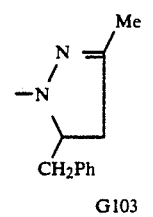
G102
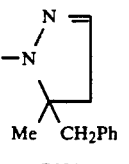
G103
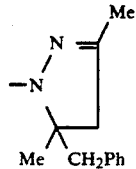
G104
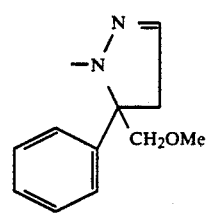
G105
G106

-continued

G107, G108, G109, G110, G111, G112, G113, G114, G115, G116, G117, G118, G119, G120, G121, G122, G123, G124, G125, G126, G127, G128, G129, G130

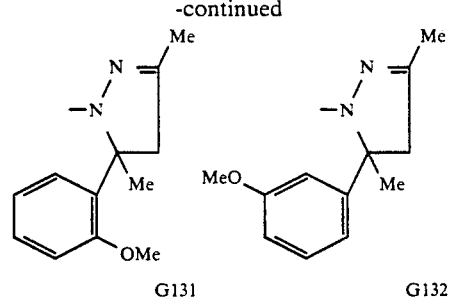
G131  G132
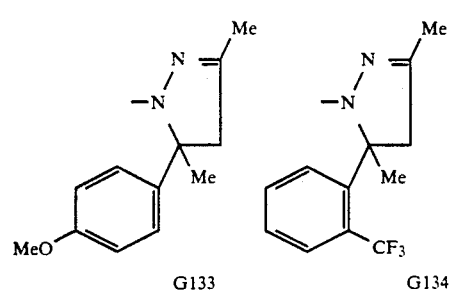
G133  G134
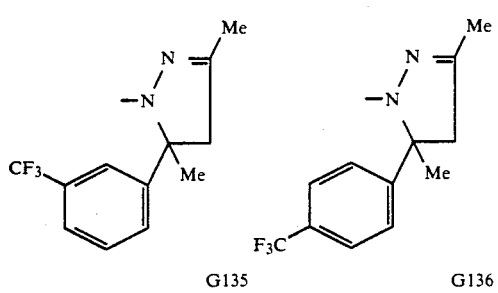
G135  G136
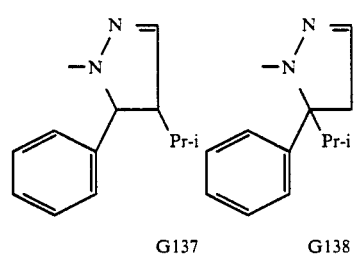
G137  G138
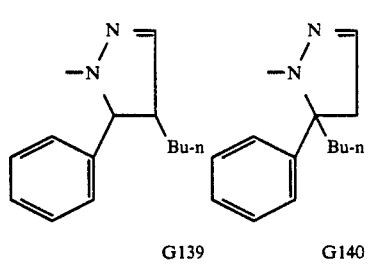
G139  G140
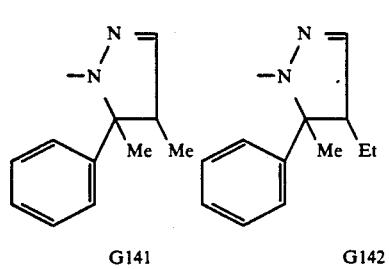
G141  G142
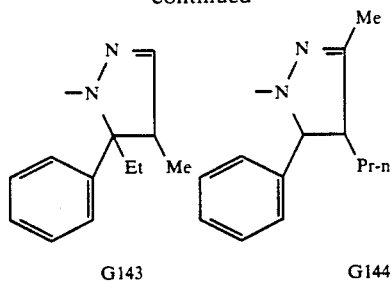
G143  G144
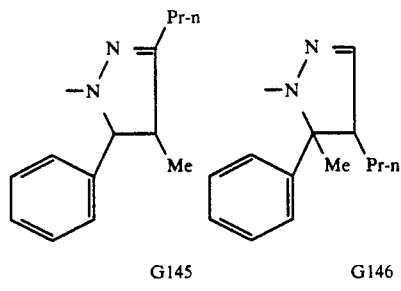
G145  G146
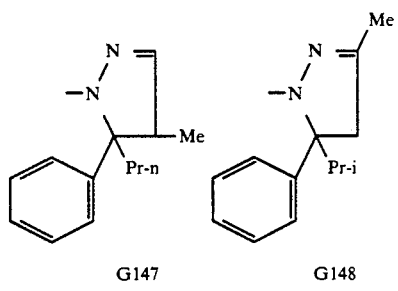
G147  G148
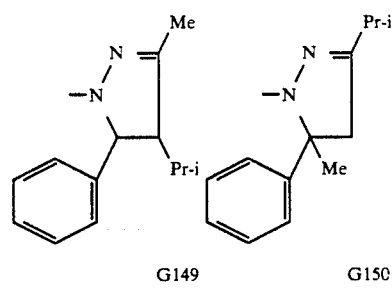
G149  G150
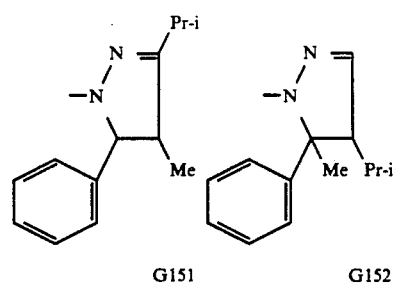
G151  G152
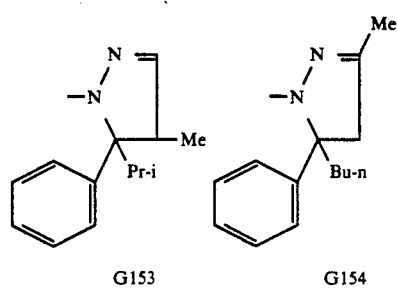
G153  G154

-continued
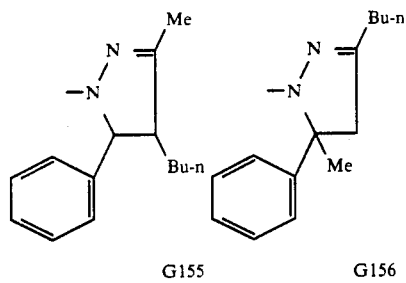
G155  G156
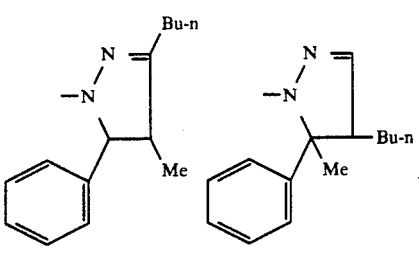
G157  G158
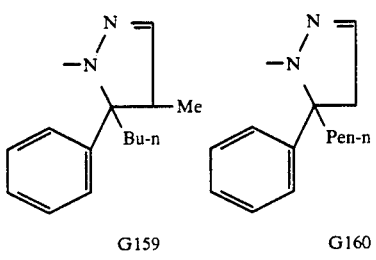
G159  G160
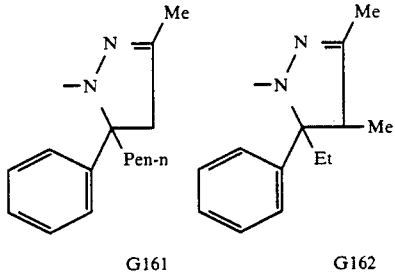
G161  G162
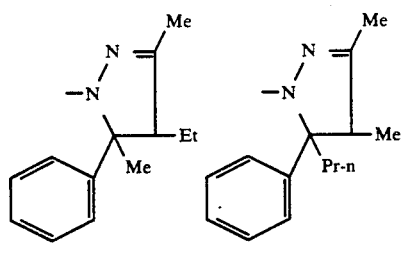
G163  G164
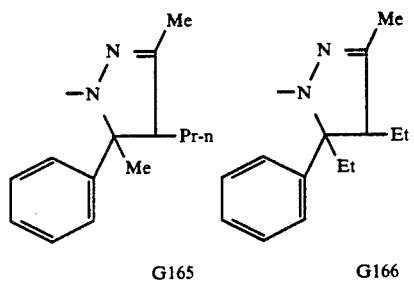
G165  G166
-continued
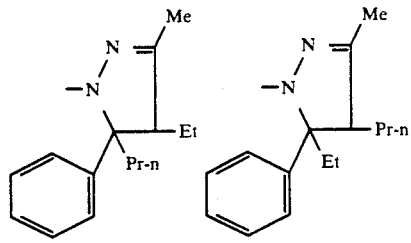
G167  G168
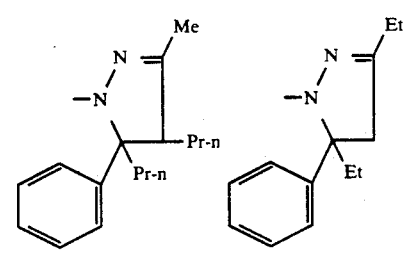
G169  G170
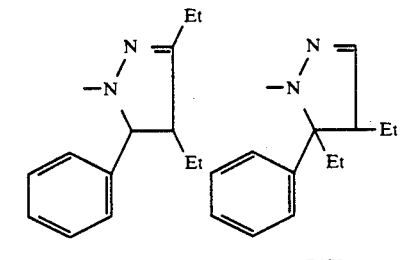
G171  G172
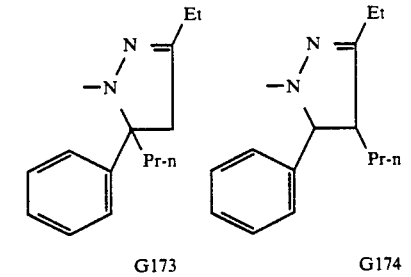
G173  G174
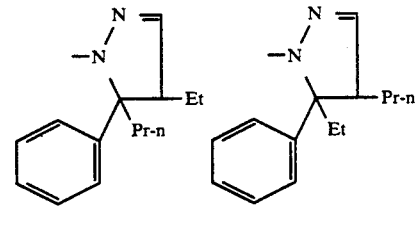
G175  G176
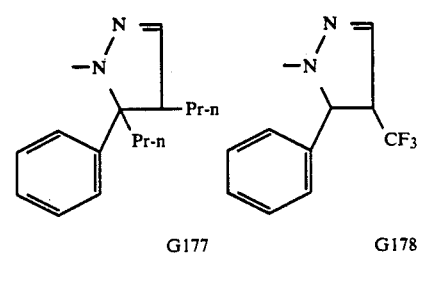
G177  G178

-continued
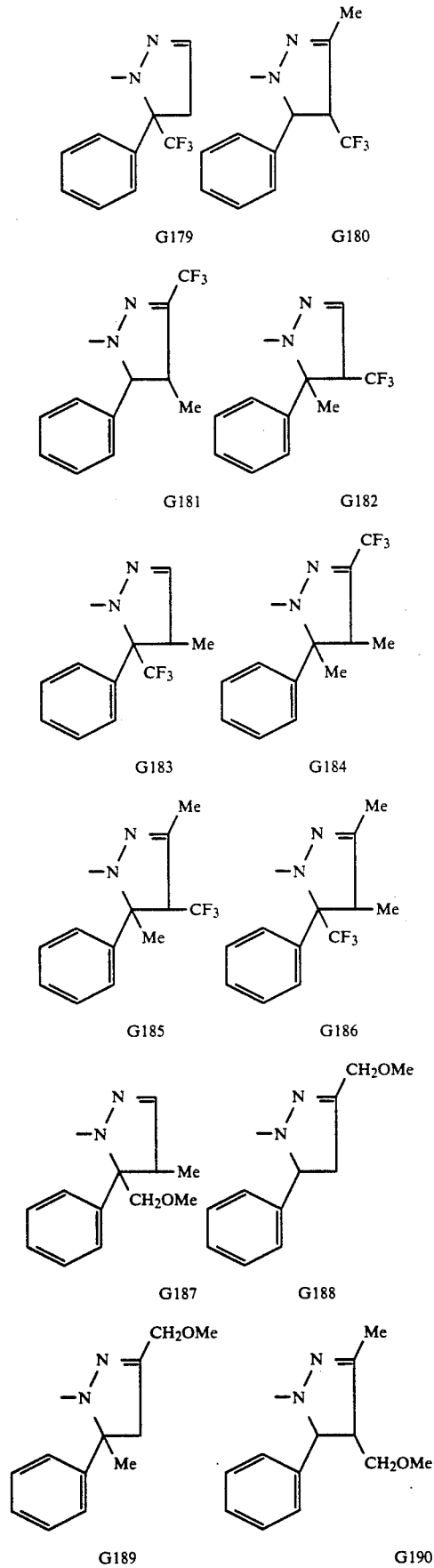
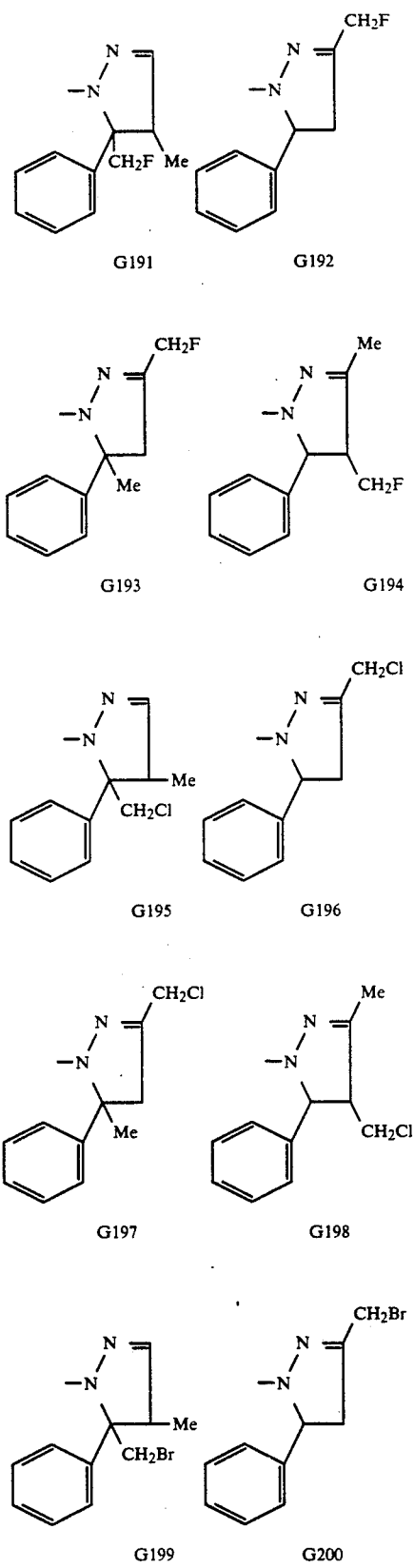

-continued
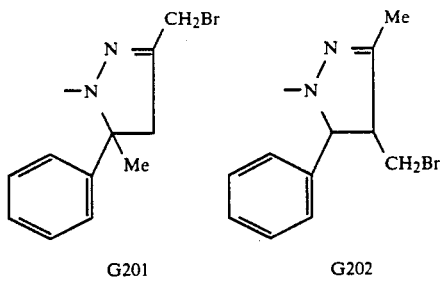
G201  G202
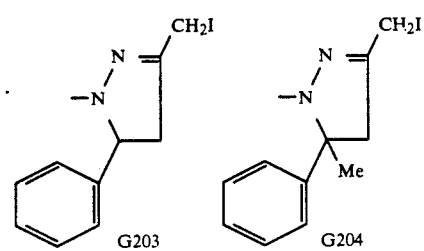
G203  G204
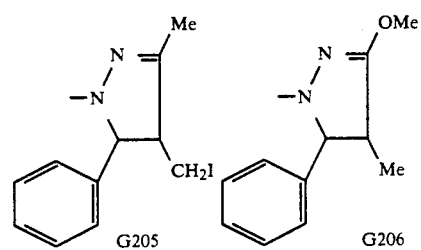
G205  G206
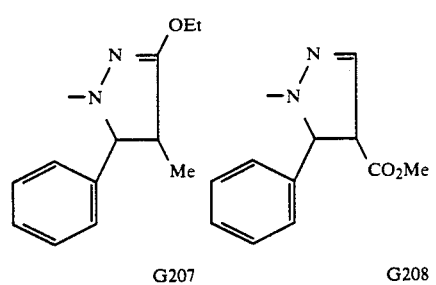
G207  G208
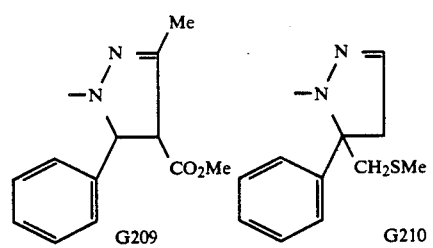
G209  G210
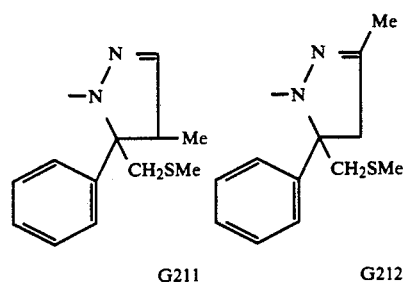
G211  G212
-continued
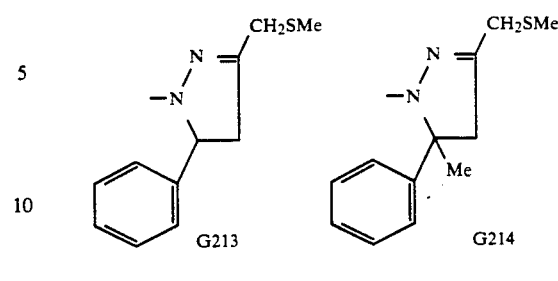
G213  G214
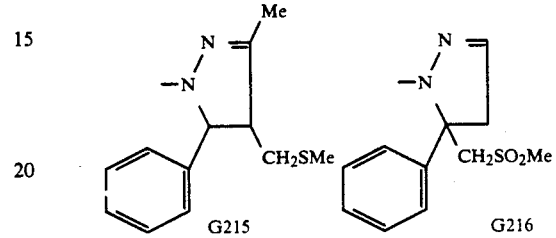
G215  G216
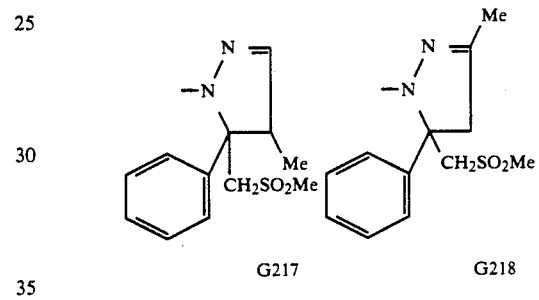
G217  G218
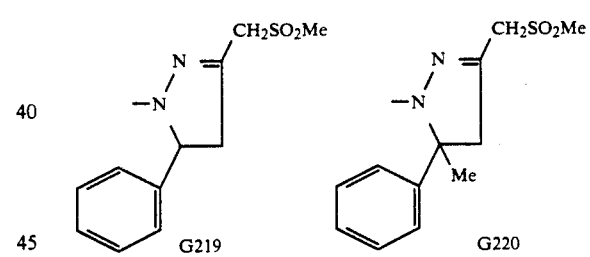
G219  G220
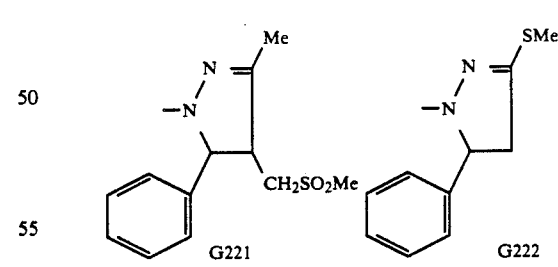
G221  G222
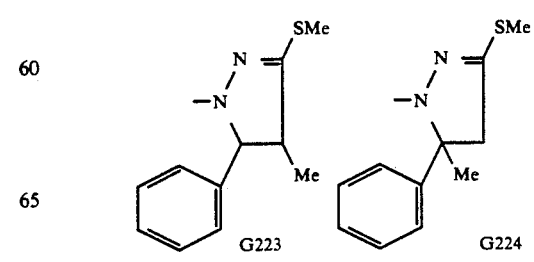
G223  G224

-continued
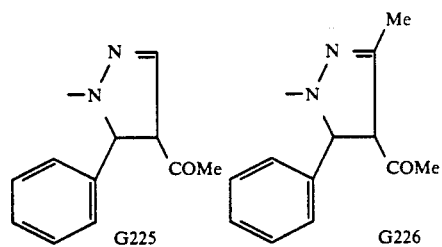
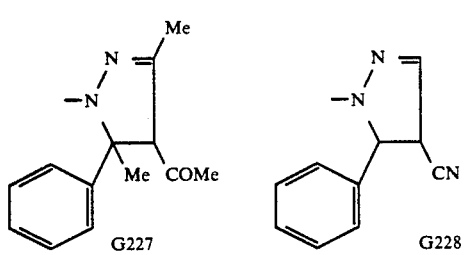
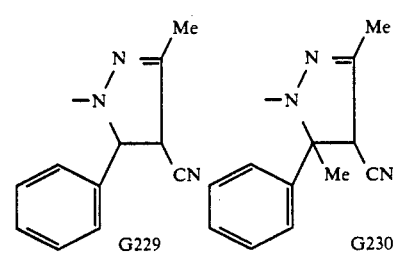
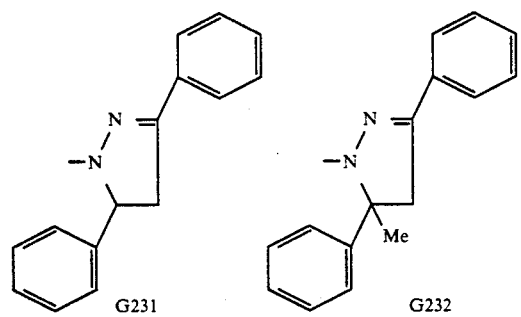
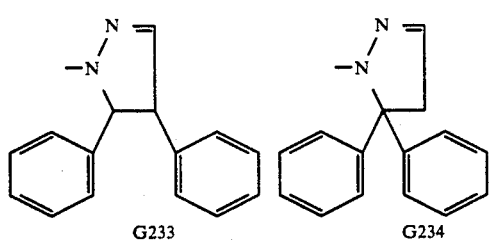
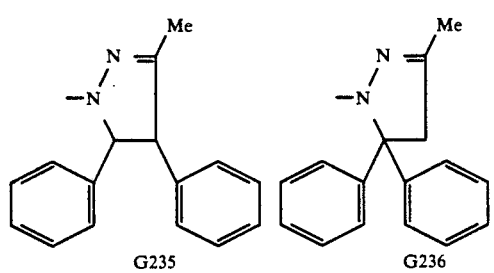
-continued
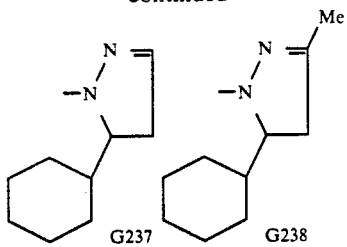
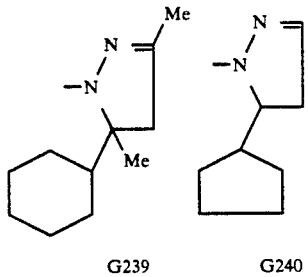
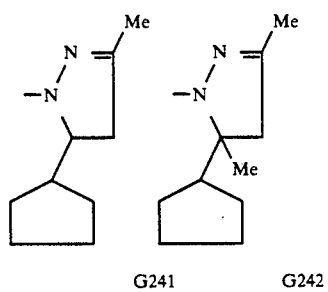
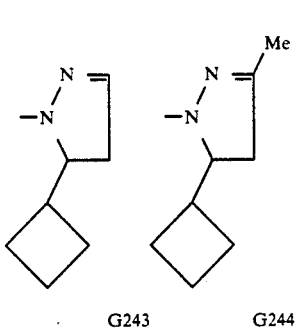
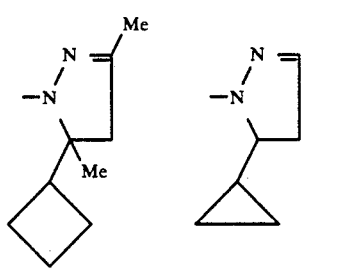

-continued
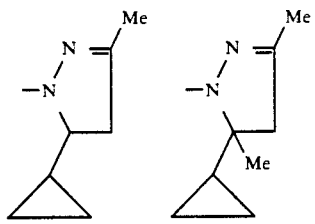
G247　　G248
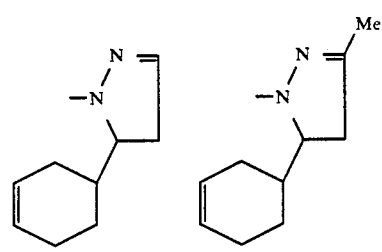
G249　　G250
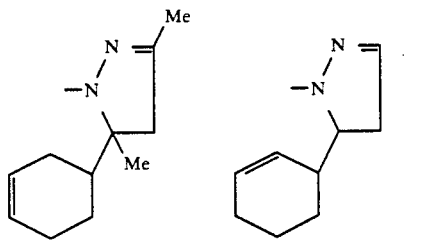
G251　　G252
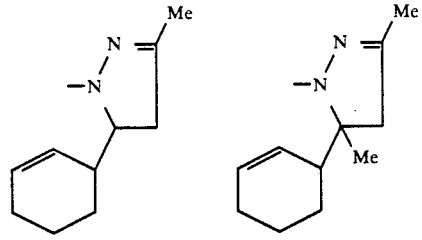
G253　　G254
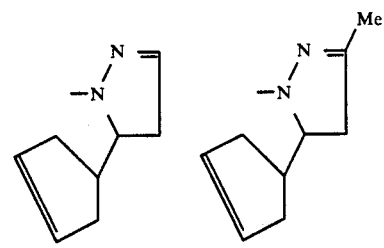
G255　　G256
-continued
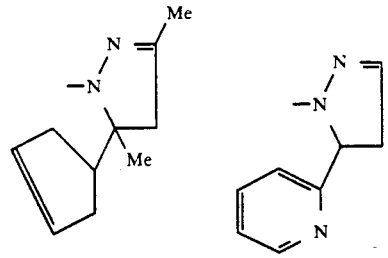
G257　　G258
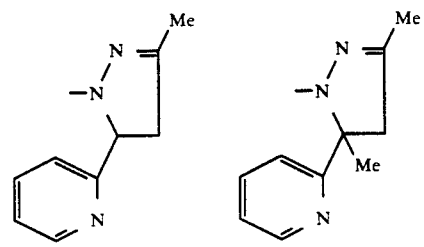
G259　　G260
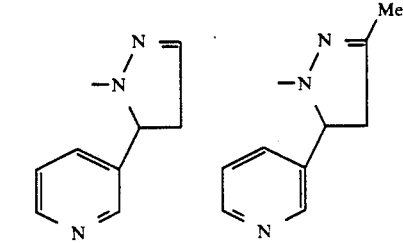
G261　　G262
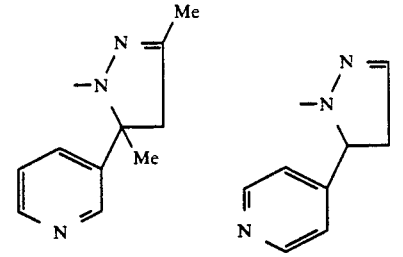
G263　　G264
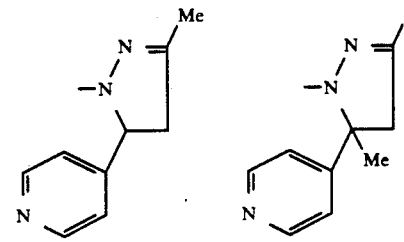
G265　　G266

-continued
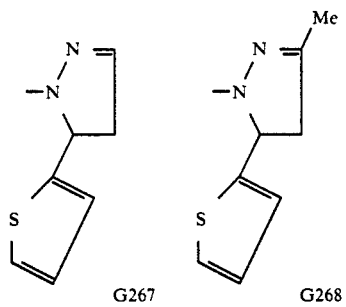
G267　　G268
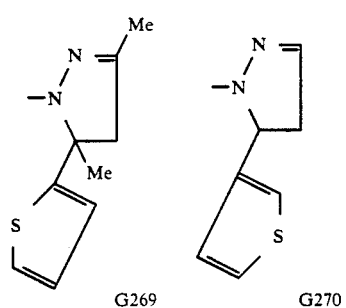
G269　　G270
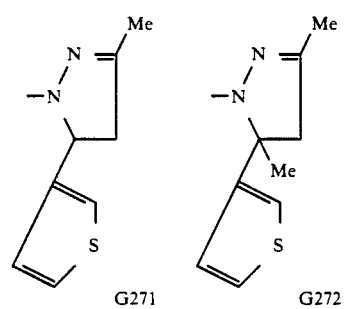
G271　　G272
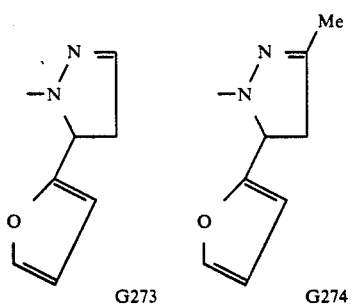
G273　　G274
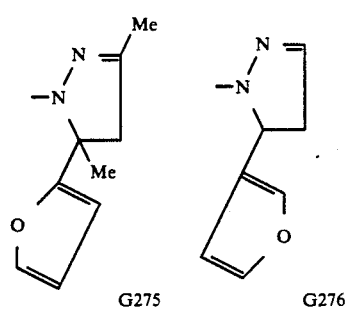
G275　　G276
-continued
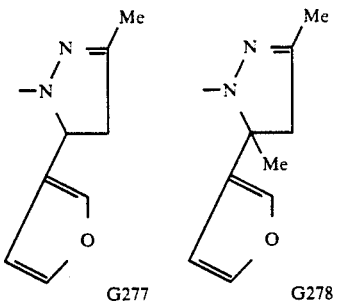
G277　　G278
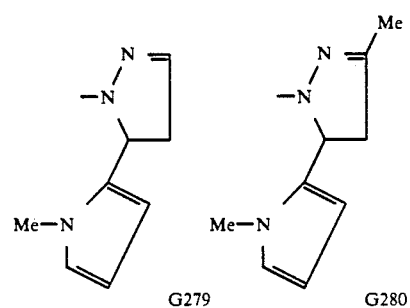
G279　　G280
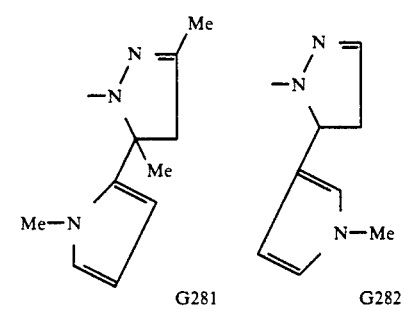
G281　　G282
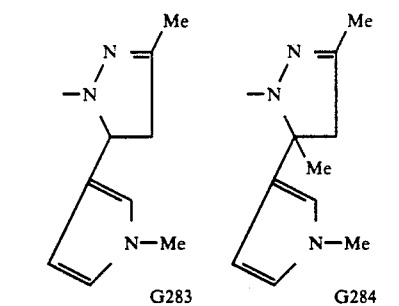
G283　　G284
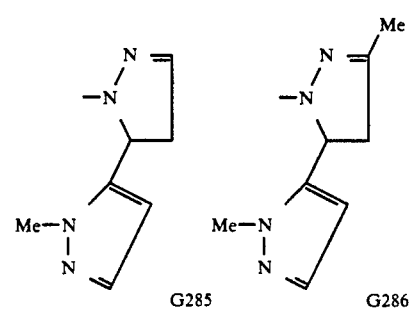
G285　　G286

-continued
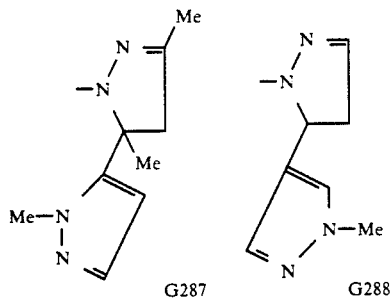
G287　G288
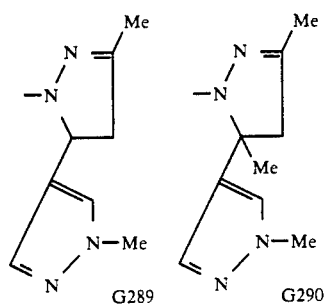
G289　G290
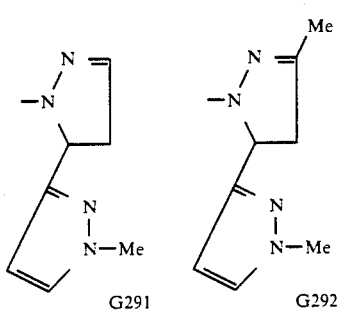
G291　G292
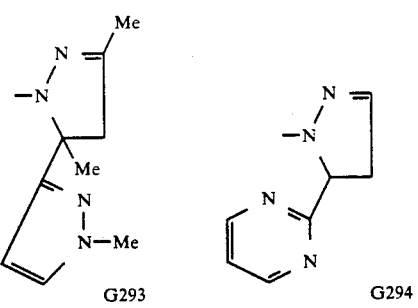
G293　G294
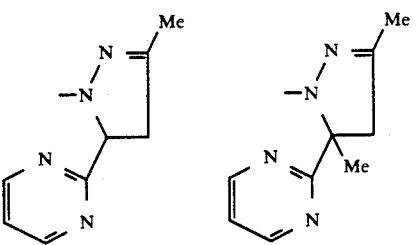
G295　G296
-continued
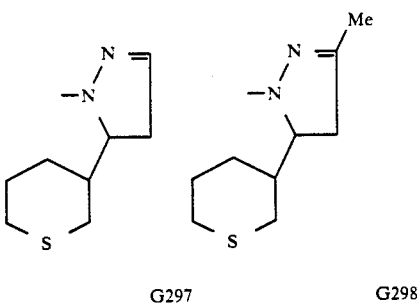
G297　G298
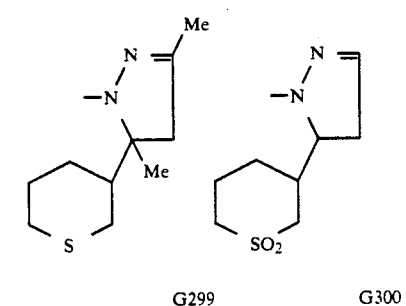
G299　G300
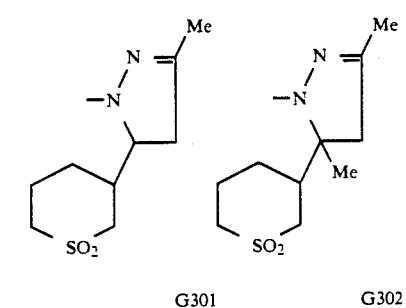
G301　G302
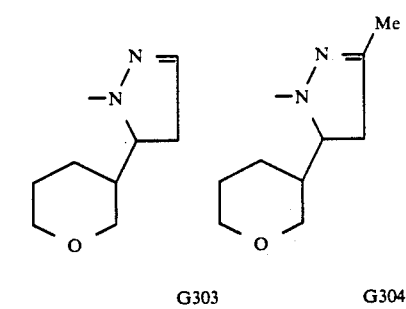
G303　G304
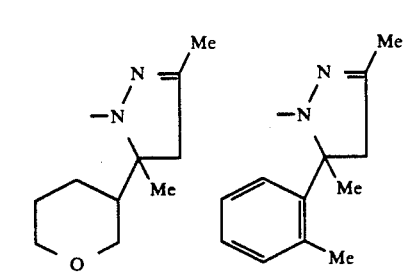
G305　G306

-continued
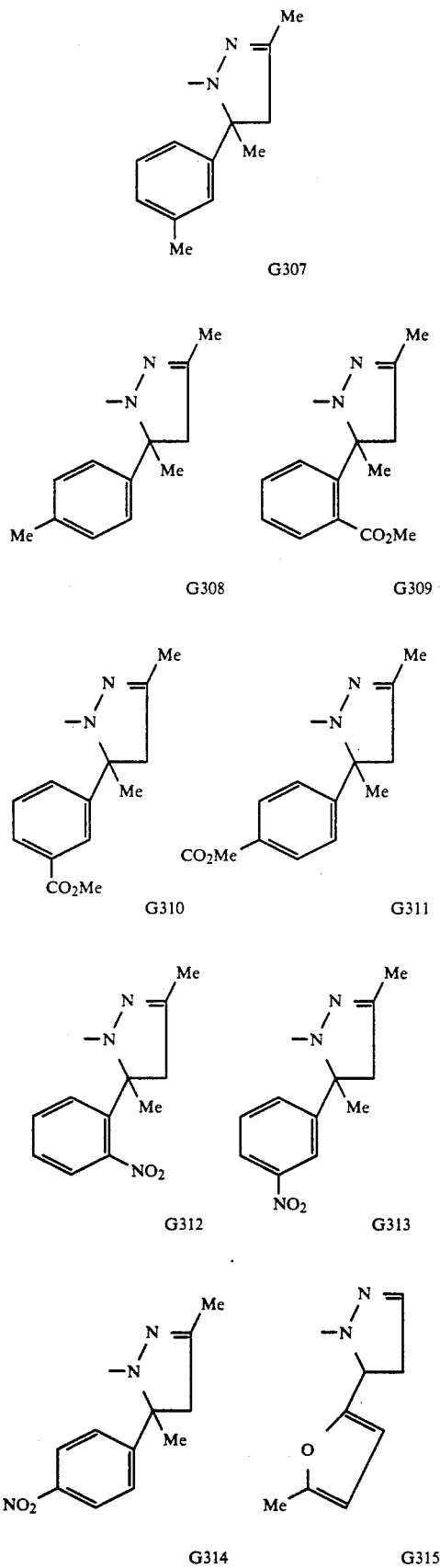
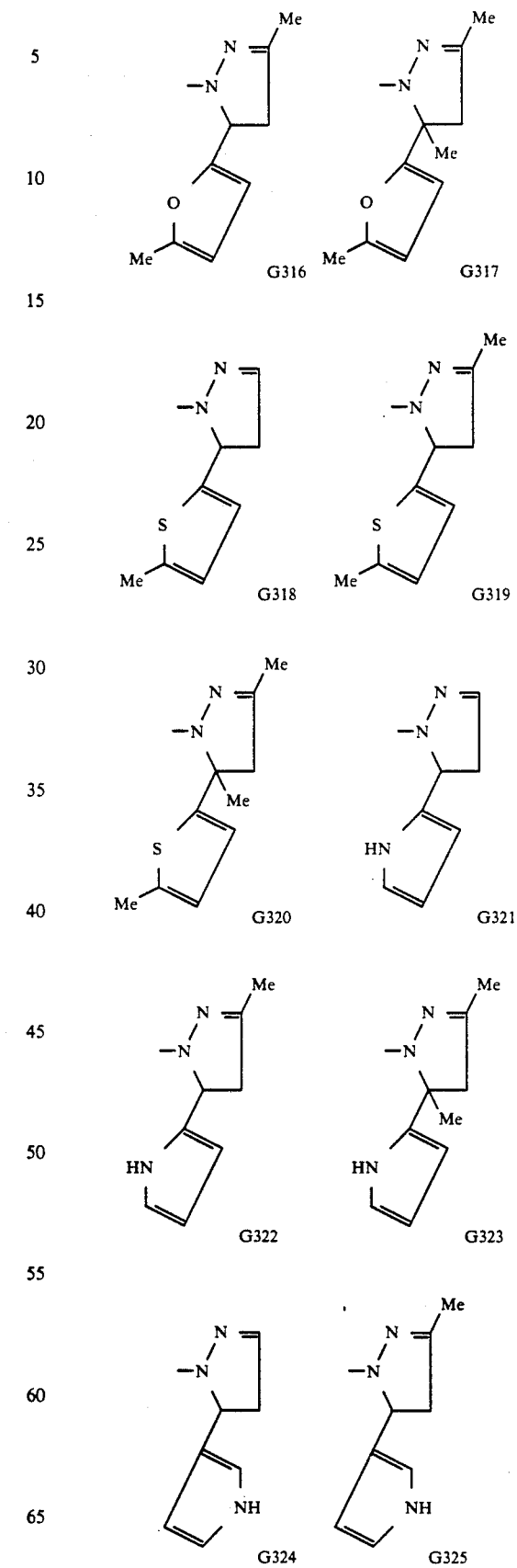

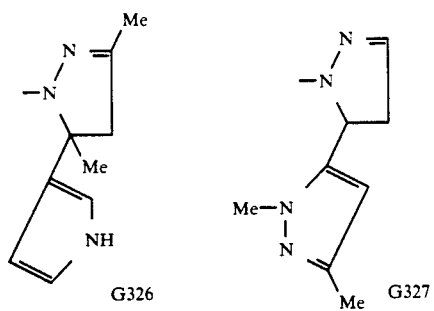
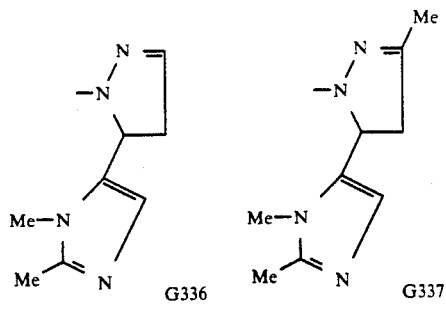
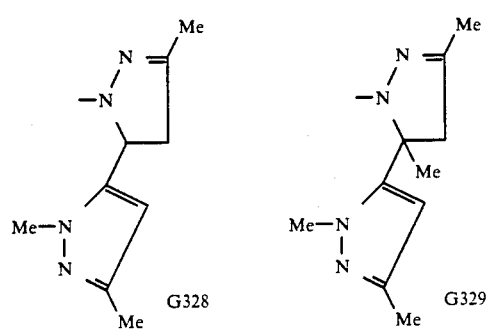
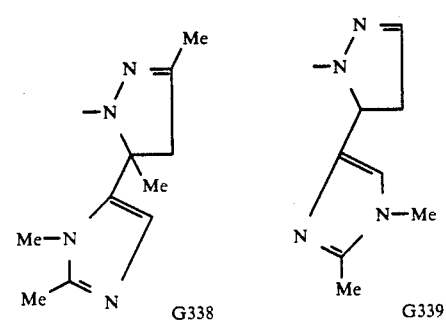
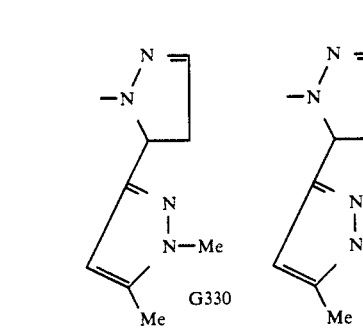
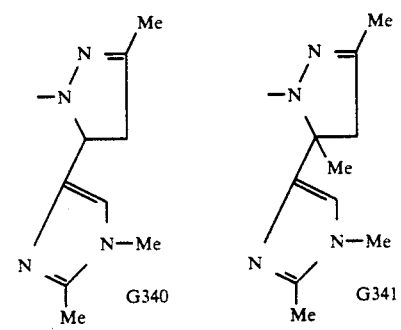
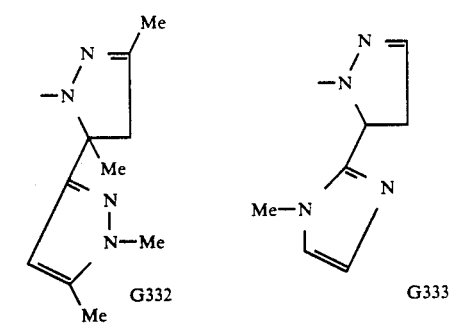
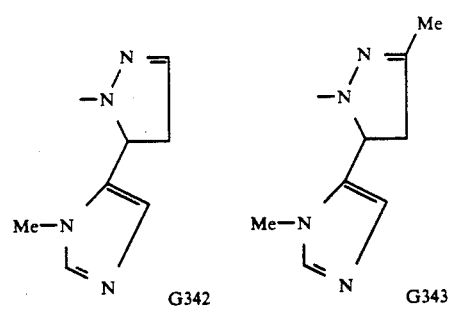
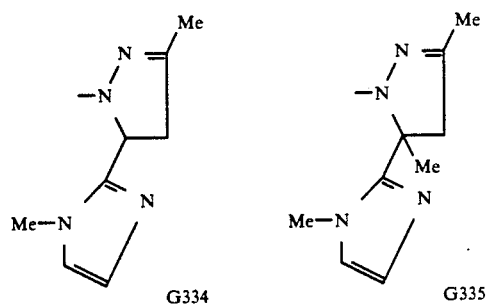
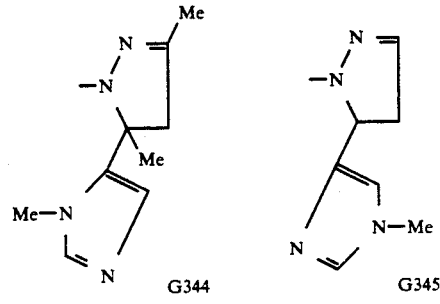

-continued
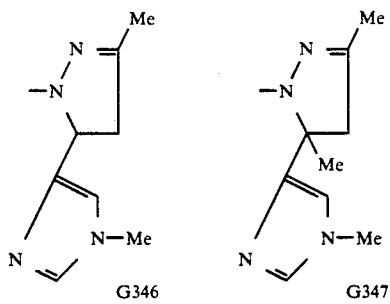
G346  G347
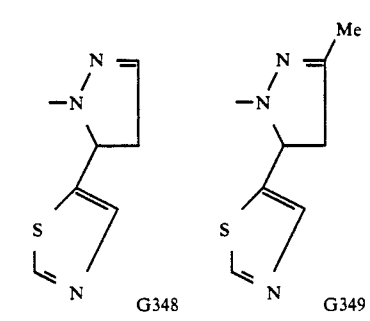
G348  G349
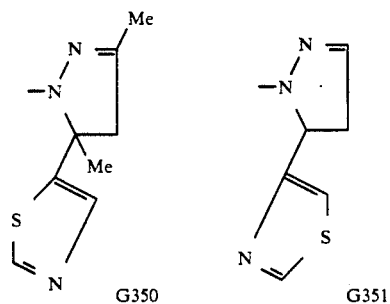
G350  G351
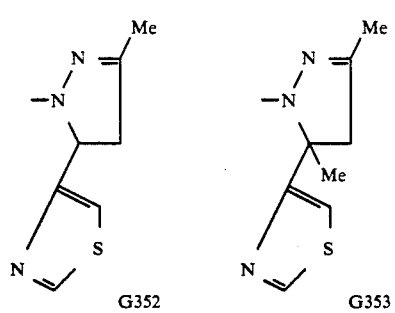
G352  G353
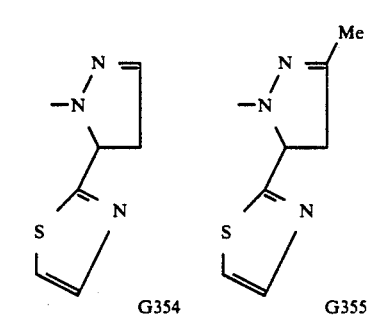
G354  G355
-continued
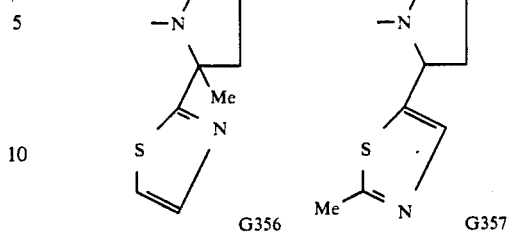
G356  G357
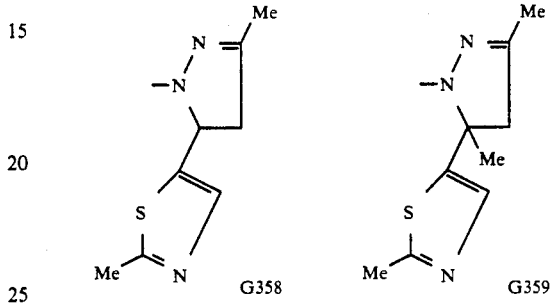
G358  G359
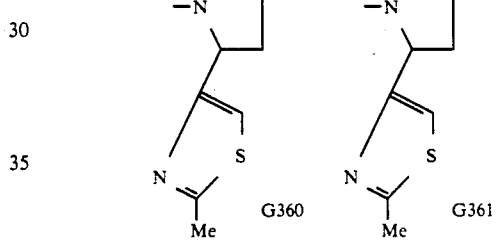
G360  G361
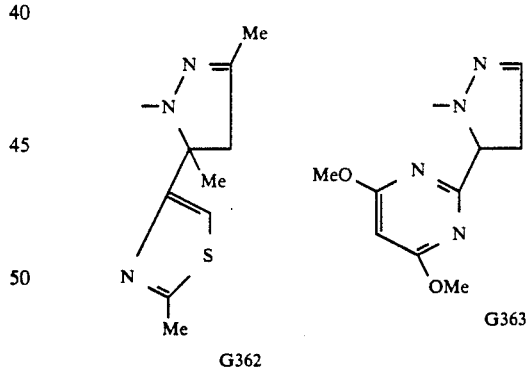
G362  G363
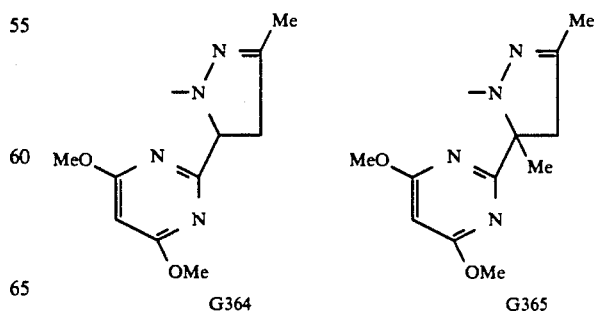
G364  G365

-continued
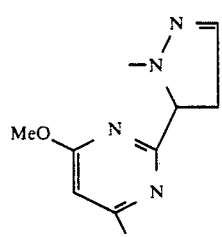
G366
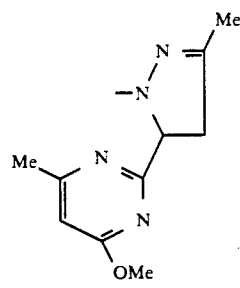
G367
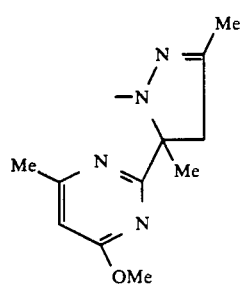
G368
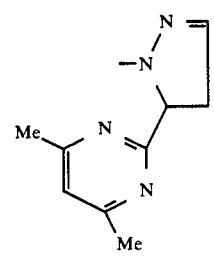
G369
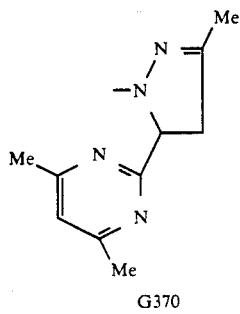
G370
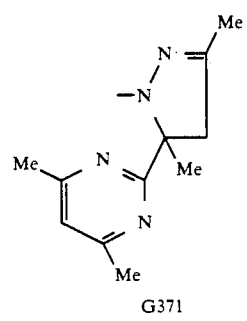
G371
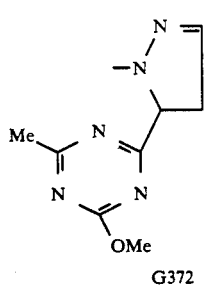
G372
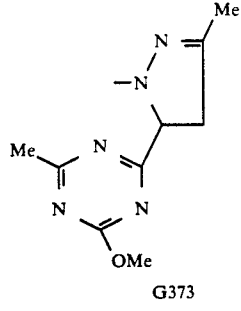
G373
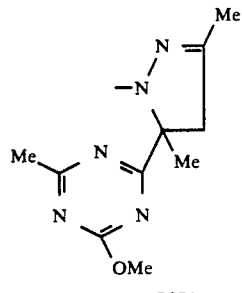
G374
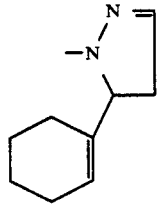
G375
-continued
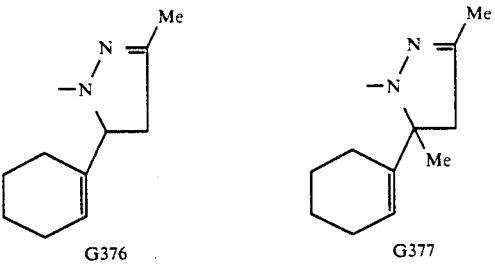
G376
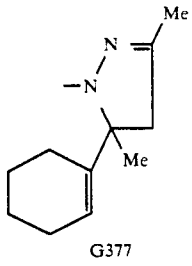
G377
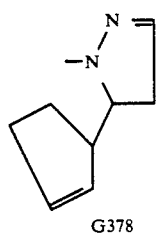
G378
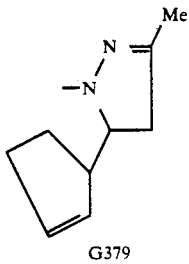
G379
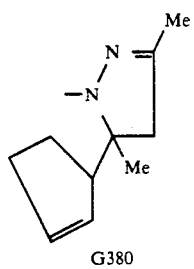
G380
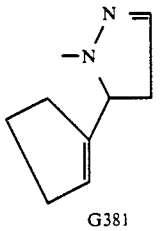
G381
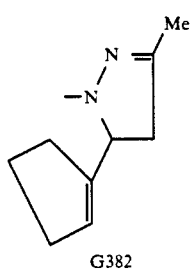
G382
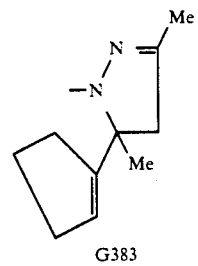
G383
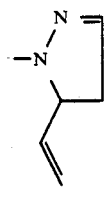
G384
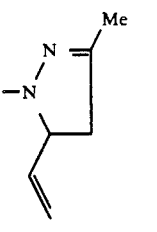
G385
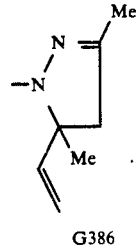
G386
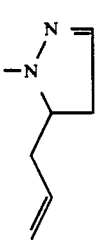
G387

-continued
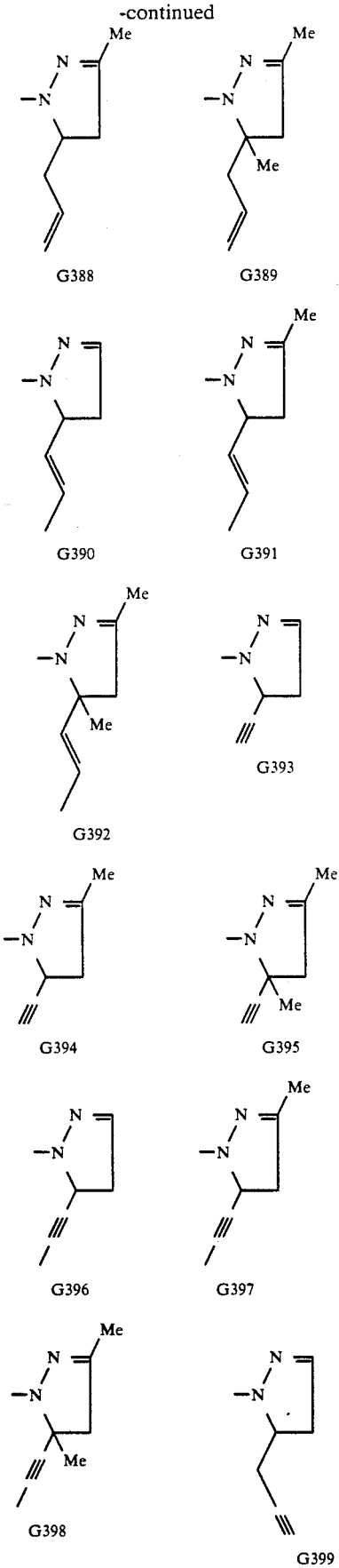
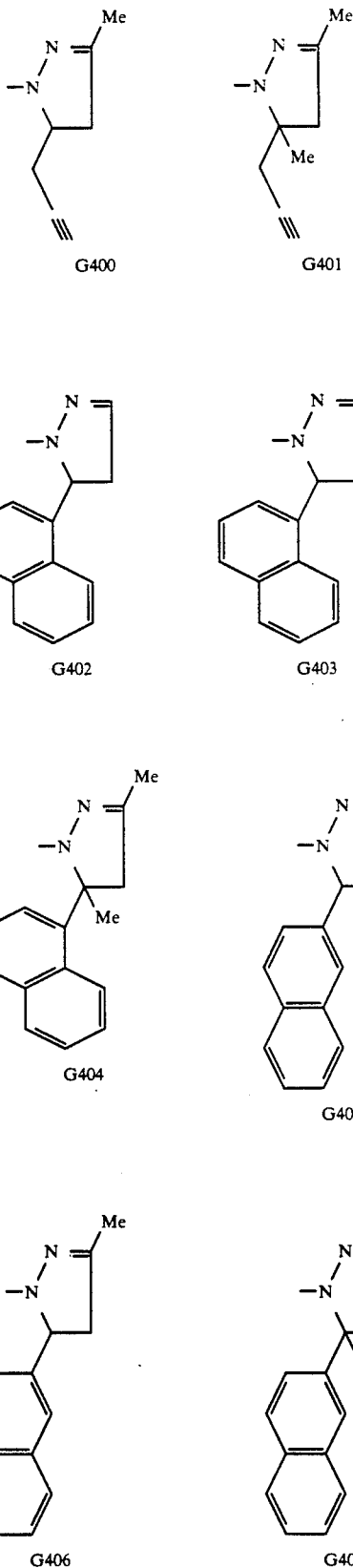

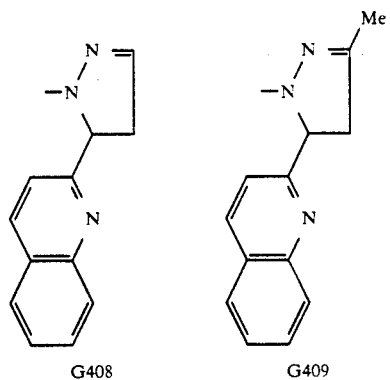
G408   G409
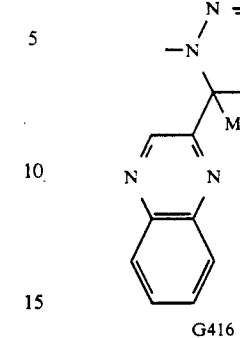
G416
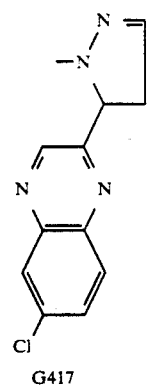
G417
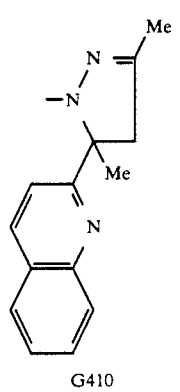
G410   G411
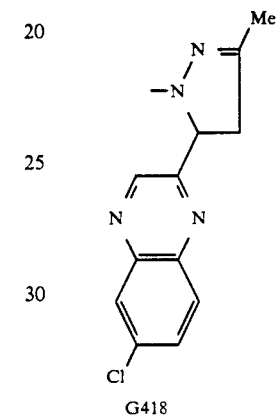
G418
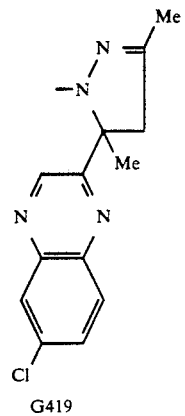
G419
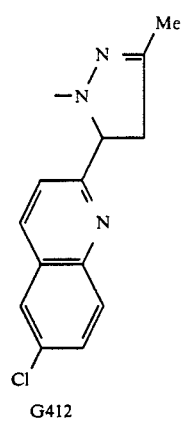
G412   G413
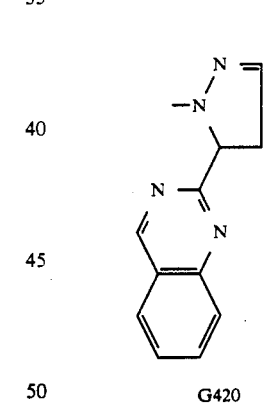
G420
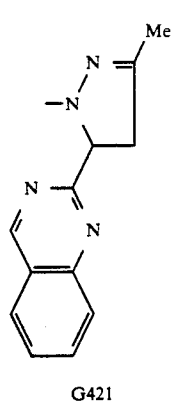
G421
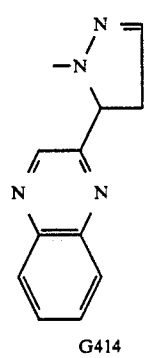
G414   G415
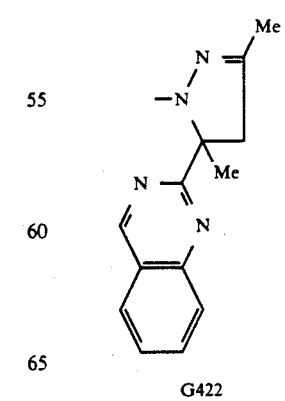
G422
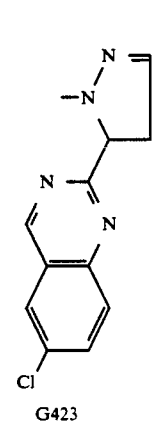
G423

-continued
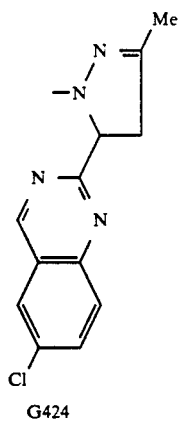 G424
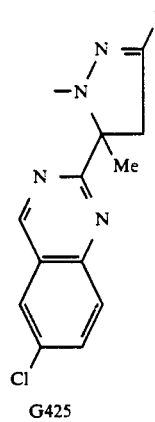 G425
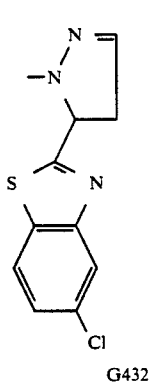 G432
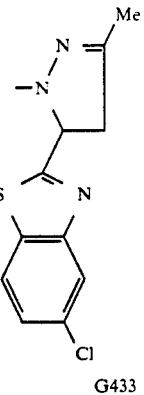 G433
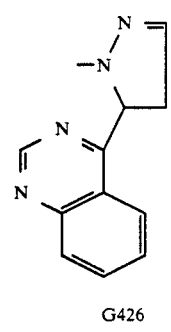 G426
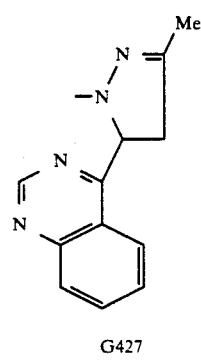 G427
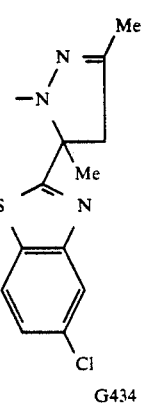 G434
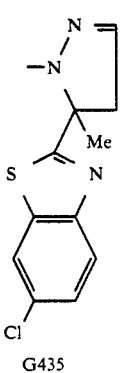 G435
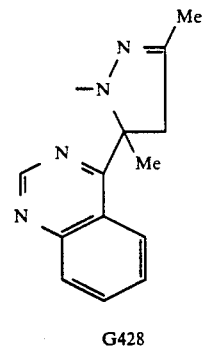 G428
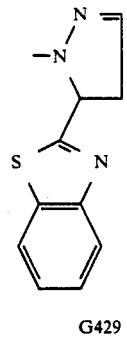 G429
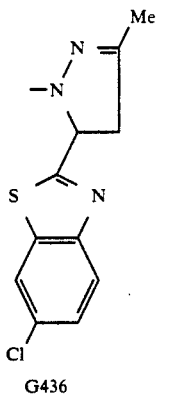 G436
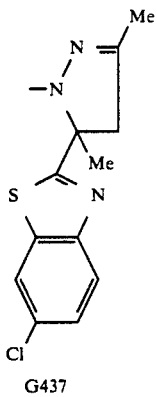 G437
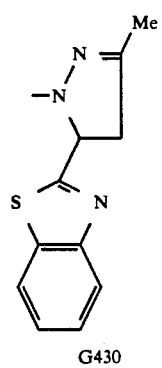 G430
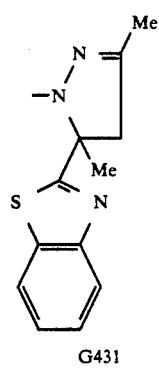 G431
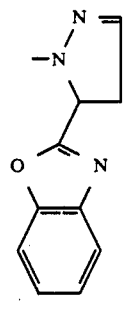 G438
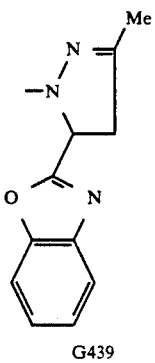 G439

-continued
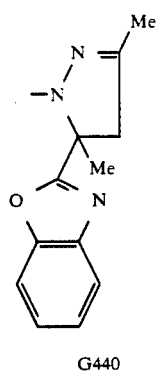
G440
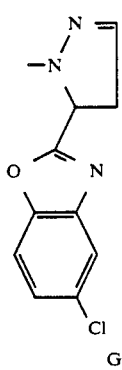
G441
-continued
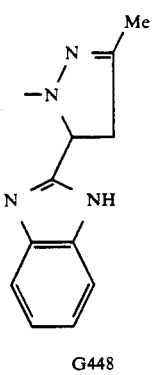
G448
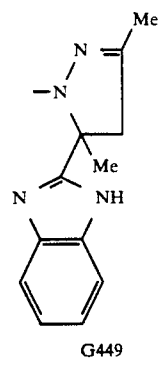
G449
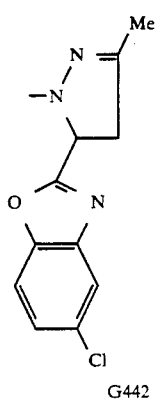
G442
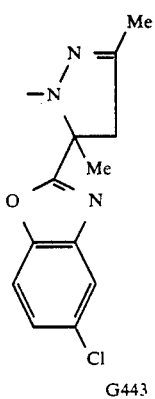
G443
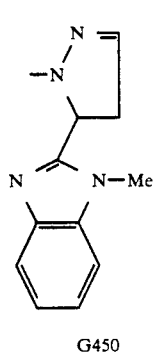
G450
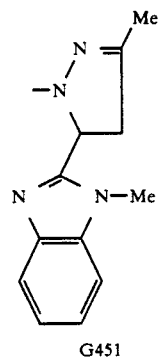
G451
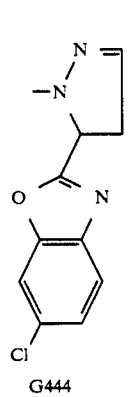
G444
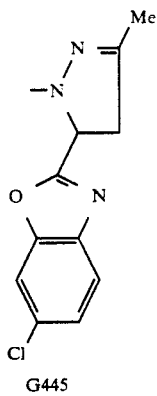
G445
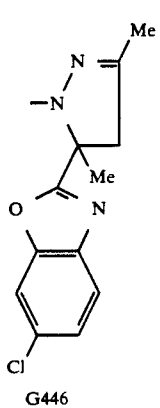
G446
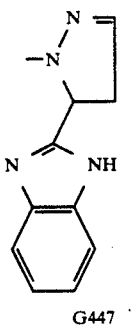
G447
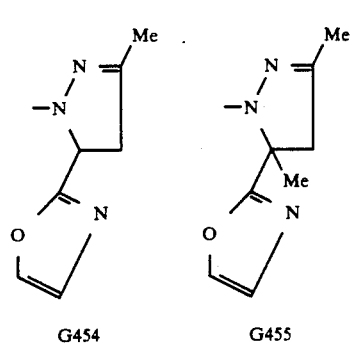
G452  G453
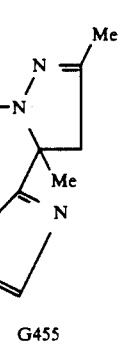
G454  G455

-continued
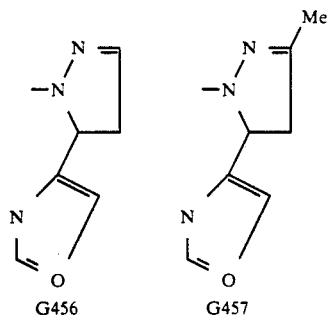
G456  G457
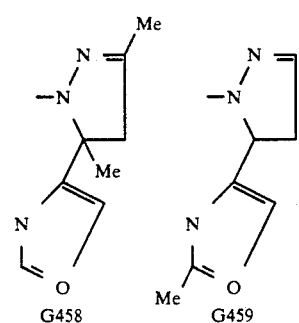
G458  G459
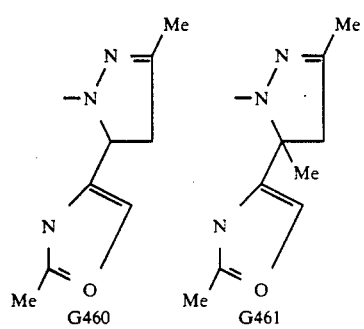
G460  G461
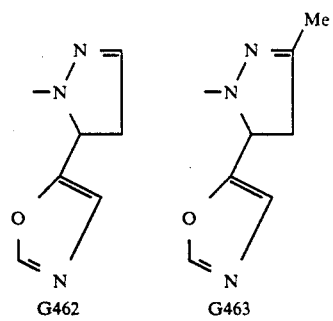
G462  G463
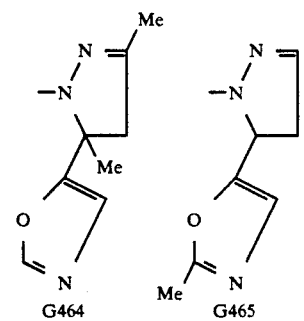
G464  G465
-continued
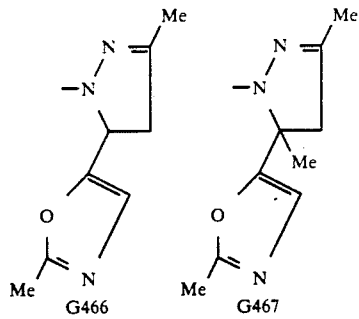
G466  G467
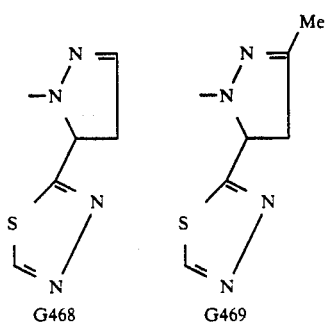
G468  G469
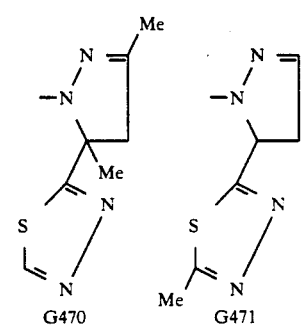
G470  G471
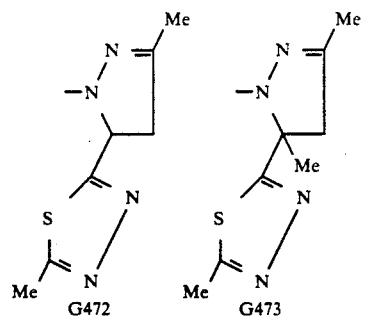
G472  G473
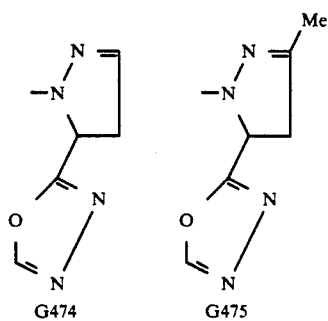
G474  G475

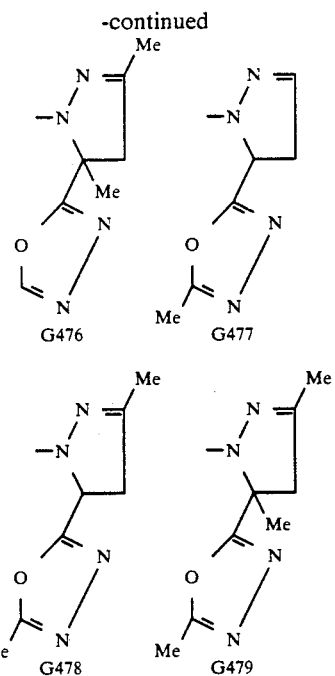

When the compound of the present invention is to be used as a herbicide, it is usually mixed with a suitable carrier, for instance, a solid carrier such as clay, talc, bentonite or diatomaceous earth, or a liquid carrier such as water, an alcohol (such as methanol or ethanol), an aromatic hydrocarbon (such as benzene, toluene or xylene), a chlorinated hydrocarbon, an ether, a ketone, an ester (such as ethyl acetate), or an acid amide (such as N,N-dimethylformamide). If desired, an emulsifier, a dispersing agent, a suspending agent, a penetrating agent, a spreader or a stabilizer may be added to prepare an optional formulation such as a liquid formulation, an emulsifiable concentrate, a wettable powder, a dust, a granule or a flowable.

Now, Formulation Examples of the herbicides containing the compounds of the present invention as active ingredients, will be given. However, it should be understood that the present invention is by no means restricted to such specific Examples. In the following Formulation Examples, "parts" means "parts by weight".

| FORMULATION EXAMPLE 1: Wettable powder | |
|---|---|
| Compound No. 1 of the present invention | 20 parts |
| Zeeklite A (tradename for a kaolin-type clay, manufactured by Zeeklite Industries, Co., Ltd.) | 76 parts |
| Sorpol 5039 (tradename for a mixture of a nonionic surfactant and an anionic surfactant, manufactured by Toho Chemical Industry Co., Ltd.) | 2 parts |
| Carplex (tradename for a coagulation-preventing agent composed of a mixture of a surfactant and fine silica powder, manufactured by Shionogi Pharmaceutical Co., Ltd.) | 2 parts |

The above ingredients are homogeneously pulverized and mixed to form a wettable powder.

| FORMULATION EXAMPLE 2: Wettable powder | |
|---|---|
| Compound No. 3 of the present invention | 40 parts |
| Zeeklite A (tradename for a kaolin-type clay, manufactured by Zeeklite Industries, Co., Ltd.) | 54 parts |
| Sorpol 5039 (tradename for a mixture of a nonionic surfactant and an anionic surfactant, manufactured by Toho Chemical Industry Co., Ltd.) | 2 parts |
| Carplex (tradename for a coagulation-preventing agent composed of a mixture of a surfactant and fine silica powder, manufactured by Shionogi Pharmaceutical Co., Ltd.) | 4 parts |

The above ingredients are homogeneously pulverized and mixed to form a wettable powder.

| FORMULATION EXAMPLE 3: Emulsifiable concentrate | |
|---|---|
| Compound No. 19 of the present invention | 5 parts |
| Xylene | 75 parts |
| N,N-dimethylformamide | 15 parts |
| Sorpol 2680 (tradename for a mixture of a nonionic surfactant and an anionic surfactant, manufactured by Toho Chemical Industry Co., Ltd.) | 5 parts |

The above ingredients are homogeneously mixed to form an emulsifiable concentrate. In its use, the above emulsifiable concentrate is diluted with water from 10 to 10,000 times and applied so that the active ingredient will be from 0.0005 to 10 kg per hectare.

| FORMULATION EXAMPLE 4: Flowable | |
|---|---|
| Compound No. 21 of the present invention | 25 parts |
| Agrizole S-710 (tradename for a nonionic surfactant, manufactured by Kao Corp.) | 10 parts |
| Runox 1000C (tradename for an anionic surfactant, manufactured by Toho Chemical Industry Co., Ltd.) | 0.5 part |
| 1% Rodopol water (tradename for a thickener, manufactured by Rhone-Poulenc) | 20 parts |
| Water | 44.5 parts |

The above ingredients were homogeneously mixed to obtain a flowable.

| FORMULATION EXAMPLE 5: Flowable | |
|---|---|
| Compound No. 3 of the present invention | 40 parts |
| Agrizole S-710 (tradename for a nonionic surfactant, manufactured by Kao Corp.) | 10 parts |
| Runox 1000C (tradename for an anionic surfactant, manufactured by Toho Chemical Industry Co., Ltd.) | 0.5 part |
| 1% Rodopol water (tradename for a thickener, manufactured by Rhone-Poulenc) | 20 parts |
| Water | 29.5 parts |

The above ingredients were homogeneously mixed to obtain a flowable.

| FORMULATION EXAMPLE 6: Granule | |
|---|---|
| Compound No. 13 of the present invention | 1 part |
| Bentonite | 55 parts |
| Talc | 44 parts |

The above ingredients were homogeneously mixed and pulverized, and after an addition of a small amount of water, the mixture was stirred, mixed and granulated by an extrusion-type granulating machine, followed by drying to obtain a granule.

Further, the compound of the present invention may be combined with other herbicides, various insecticides, fungicides and synergism agents at the time of the preparation of the formulations or at the time of the application, as the case requires.

As such other herbicides, compound disclosed in Farm Chemicals Handbook (1989) may, for example, be mentioned.

The compound of the present invention can be applied to control various weeds not only in the agricultural and horticultural fields such as upland fields, paddy fields or orchards, but also in non-agricultural fields such as play grounds, non-used vacant fields or railway sides.

The dose varies depending upon the application site, the season for application, the manner of application, the type of weeds to be controlled, the type of crop plants, etc. However, the dose is usually within a range of from 0.005 to 10 kg per hectare as the amount of the active ingredient.

Now, the herbicidal activities of the compounds of the present invention will be described in detail with reference to the following Test Examples. The Compound Nos. referred to in the Test Examples correspond to the Compound Nos. given above.

TEST EXAMPLE 1

Test on the herbicidal effects in soil treatment

A plastic box having a length of 15 cm, a width of 22 cm and a depth of 6 cm was filled with a sterilized diluvial soil, and seeds of *Echinochloa crus-galli, Digitaria edscendens, Cyperus microiria, Solanum nigrum, Galinsoga ciliata, Rorippa indica, Oryza sativa, Zea mays, Triticum aestivum, Glycine max* and *Gossypium herbaceum* were sown, and the soil was covered thereon in the thickness of about 1.5 cm, and then a herbicide solution was applied onto the surface of the soil uniformly so that the active ingredient was distributed at a predetermined concentration. The herbicide solution was prepared by diluting the wettable powder as described in the foregoing Formulation Examples with water and applied onto the entire soil surface by means of a small spray. Four weeks after the application of the herbicidal solution, the herbicidal effects against each weed and the phytotoxicities against each crop plant were determined on the basis of the following standard ratings. The results are shown in Table 2. (Compound Nos. correspond to Compound Nos. in the Examples.) Some of the compounds of the present invention exhibit selectivity for certain crop plants.

Standard ratings:
5: Growth control rate of more than 90% (almost completely withered)
4: Growth control rate of from 70 to 90%
3: Growth control rate of from 40 to 70%
2: Growth control rate of from 20 to 40%
1: Growth control rate of from 5 to 20%
0: Growth control rate of less than 5% (almost non-effective)

The above growth control rates were calculated by the following equation:

$$\text{Growth control rate } (\%) = \left(1 - \frac{T}{N}\right) \times 100$$

where
T: Weight of the weed grown above the soil surface of the treated area
N: Weight of the weed grown above the soil surface of the non-treated area

TEST EXAMPLE 2

Test on the herbicidal effects in foliage treatment

A plastic box having a length of 15 cm, a width of 22 cm and a depth of 6 cm was filled with a sterilized diluvial soil, and seeds of *Echinochloa crus-galli, Digitaria adscendens, Cyperus microiria, Solanum nigrum, Galinsoga ciliata, Rorippa indica, Oryza sativa, Zea mays, Triticum aestivum, Glycine max, Gossypium herbaceum* and *Beta vulgaris* were spot-wisely sown, and the soil was covered thereon in a thickness of about 1.5 cm. When the various weeds and crop plants grew to the 2 or 3 leaf stage, a herbicidal solution was uniformly sprayed on the foliages so that the active ingredient was applied in a predetermined concentration.

The herbicidal solution was prepared by diluting the wettable powder as described in the above Formulation Examples with water and applied onto the entire surface of the foliages of the weeds and the crop plants by a small spray. Four weeks after the application of the herbicide solution, the herbicidal effects against each weed and the phytotoxicities against each crop plant were determined on the basis of the standard ratings described in Test Example 1. The results are shown in Table 3. (Compound Nos. correspond to Compound Nos. in the Examples.)

TEST EXAMPLE 3

Test on the phytotoxicity against Triticum aestivum

A plastic box having a length of 15 cm, a width of 22 cm and a depth of 6 cm was filled with a sterilized diluvial soil, and seeds of *Triticum aestivum, Avena fatua* and *Alopecurus myosuroides* were spot-wisely sown, and the soil was covered thereon in a thickness of 1 cm.

When the plants grew to the 2 or 3 leaf stage, a herbicidal solution was uniformly sprayed on the foliages so that the active ingredient was applied in a predetermined concentration by a small spray. Twenty days after the treatment, the herbicidal effects against weeds and the phytotoxicity against Triticum aestivum were determined on the basis of the standard ratings described in Test Example 1. The results are shown in Table 4. (Compound Nos. correspond to Compound Nos. in the Examples.)

In Tables 2, 3 and 4, the following abbreviations are used.
Dose: Dose of active ingredient
EC: Echinochloa crus-galli (barnyardgrass)
DI: Digitaria adscendens (large crabgrass)
CY: Cyperus microiria (annual sedge)
SO: Solanum nigrum (black nightshade)
GA: Galinsoga ciliata (hairy galinsoga)
RO: Rorippa indica (fieldcress)
OR: Oryza sativa (rice)
ZE: Zea mays (corn)
TR: Triticum aestivum (wheat)
GL: Glycine max (soybean)

GO: Gossypium herbaceum (cotton)
BE: Beta vulgaris (sugar beet)
AV: Avena fatua (wild oat)
AL: Alopecurus myosuroides (blackgrass)

TABLE 2

| Comp. No. | Dose kg/ha | EC | DI | CY | SO | GA | RO | OR | ZE | TR | GL | GO |
|---|---|---|---|---|---|---|---|---|---|---|---|---|
| 1 | 0.16 | 3 | 4 | 2 | 5 | 5 | 5 | 5 | 1 | 2 | 1 | 1 |
|   | 0.32 | 4 | 5 | 4 | 5 | 5 | 5 | 5 | 2 | 3 | 2 | 3 |
|   | 0.63 | 5 | 5 | 5 | 5 | 5 | 5 | 5 | 3 | 4 | 3 | 4 |
| 3 | 0.16 | 2 | 3 | 3 | 4 | 5 | 5 | 3 | 0 | 0 | 1 | 2 |
|   | 0.32 | 3 | 4 | 4 | 5 | 5 | 5 | 4 | 0 | 1 | 2 | 3 |
|   | 0.63 | 4 | 5 | 5 | 5 | 5 | 5 | 5 | 0 | 2 | 4 | 4 |
| 4 | 0.63 | 3 | 4 | 3 | 5 | 5 | 5 | 4 | 0 | 2 | 1 | 1 |
| 5 | 0.63 | 4 | 5 | 3 | 4 | 5 | 5 | 5 | 1 | 0 | 1 | 2 |
| 7 | 0.16 | 1 | 2 | 1 | 5 | 5 | 5 | 4 | 0 | 0 | 0 | 0 |
|   | 0.32 | 2 | 3 | 2 | 5 | 5 | 5 | 5 | 0 | 0 | 0 | 1 |
|   | 0.63 | 3 | 4 | 4 | 5 | 5 | 5 | 5 | 1 | 1 | 1 | 2 |
| 8 | 0.63 | 3 | 5 | 4 | 5 | 5 | 5 | 4 | 1 | 0 | 2 | 1 |
| 13 | 0.16 | 1 | 1 | 2 | 5 | 5 | 5 | 2 | 0 | 0 | 0 | 1 |
|    | 0.32 | 2 | 2 | 3 | 5 | 5 | 5 | 3 | 0 | 1 | 1 | 2 |
|    | 0.63 | 3 | 4 | 4 | 5 | 5 | 5 | 4 | 0 | 2 | 2 | 3 |
| 19 | 0.63 | 3 | 2 | 3 | 5 | 5 | 5 | 0 | 0 | 0 | 1 | 1 |
| 20 | 0.63 | 2 | 1 | 1 | 4 | 5 | 5 | 0 | 2 | 1 | 2 | 1 |
| 21 | 0.63 | 2 | 1 | 1 | 5 | 5 | 5 | 4 | 1 | 3 | 3 | 3 |
| 28 | 1.6 | 3 | 4 | 4 | 4 | 5 | 5 | 4 | 1 | 1 | 2 | 2 |
|    | 3.2 | 4 | 5 | 5 | 5 | 5 | 5 | 5 | 2 | 2 | 3 | 3 |
|    | 6.3 | 5 | 5 | 5 | 5 | 5 | 5 | 5 | 3 | 3 | 4 | 4 |
| Comparative Compound A | 2.5 | 0 | 0 | 0 | 0 | 0 | 0 | 0 | 0 | 0 | 0 | 0 |
| Comparative Compound B | 2.5 | 0 | 0 | 0 | 0 | 0 | 0 | 0 | 0 | 0 | 0 | 0 |

Comparative Compounds A and B:
Disclosed in Japanese Unexamined Patent Publication No. 122671/1988

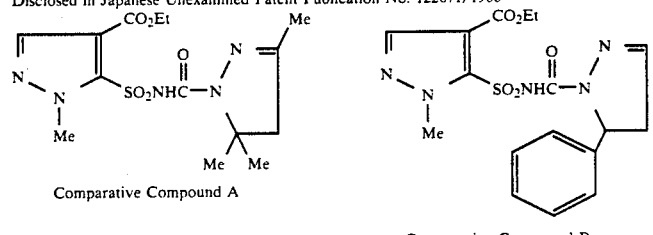

Comparative Compound A

Comparative Compound B

TABLE 3

| Comp. No. | Dose kg/ha | EC | DI | CY | SO | GA | RO | OR | ZE | TR | GL | GO | BE |
|---|---|---|---|---|---|---|---|---|---|---|---|---|---|
| 1 | 0.16 | 4 | 4 | 1 | 5 | 5 | 5 | 4 | 2 | 1 | 4 | 4 | 5 |
|   | 0.32 | 5 | 5 | 2 | 5 | 5 | 5 | 5 | 3 | 1 | 5 | 5 | 5 |
|   | 0.63 | 5 | 5 | 3 | 5 | 5 | 5 | 5 | 4 | 2 | 5 | 5 | 5 |
| 3 | 0.16 | 5 | 4 | 5 | 5 | 5 | 5 | 1 | 0 | 0 | 4 | 4 | 4 |
|   | 0.32 | 5 | 5 | 5 | 5 | 5 | 5 | 2 | 0 | 1 | 5 | 5 | 5 |
|   | 0.63 | 5 | 5 | 5 | 5 | 5 | 5 | 3 | 1 | 2 | 5 | 5 | 5 |
| 4 | 0.63 | 5 | 3 | 2 | 5 | 5 | 5 | 2 | 1 | 1 | 4 | 4 | 5 |
| 5 | 0.16 | 4 | 2 | 1 | 5 | 5 | 5 | 3 | 0 | 0 | 4 | 2 | 4 |
|   | 0.32 | 5 | 3 | 1 | 5 | 5 | 5 | 3 | 1 | 0 | 5 | 3 | 5 |
|   | 0.63 | 5 | 4 | 2 | 5 | 5 | 5 | 4 | 2 | 0 | 5 | 4 | 5 |
| 7 | 0.16 | 1 | 1 | 1 | 5 | 5 | 5 | 4 | 1 | 0 | 1 | 4 | 3 |
|   | 0.32 | 2 | 2 | 2 | 5 | 5 | 5 | 5 | 2 | 1 | 2 | 5 | 4 |
|   | 0.63 | 3 | 3 | 3 | 5 | 5 | 5 | 5 | 2 | 1 | 3 | 5 | 5 |
| 8 | 0.16 | 4 | 1 | 1 | 5 | 5 | 5 | 3 | 1 | 0 | 4 | 2 | 3 |
|   | 0.32 | 5 | 2 | 2 | 5 | 5 | 5 | 4 | 1 | 0 | 5 | 3 | 4 |
|   | 0.63 | 5 | 4 | 3 | 5 | 5 | 5 | 4 | 3 | 1 | 5 | 4 | 5 |
| 10 | 0.63 | 1 | 2 | 1 | 5 | 5 | 5 | 0 | 0 | 0 | 5 | 3 | 5 |
| 13 | 0.16 | 3 | 2 | 1 | 5 | 5 | 5 | 2 | 0 | 1 | 5 | 2 | 3 |
|    | 0.32 | 4 | 3 | 2 | 5 | 5 | 5 | 3 | 1 | 2 | 5 | 3 | 4 |
|    | 0.63 | 5 | 4 | 3 | 5 | 5 | 5 | 4 | 2 | 3 | 5 | 4 | 5 |
| 15 | 0.63 | 2 | 1 | 1 | 5 | 5 | 5 | 0 | 1 | 1 | 4 | 3 | 4 |
| 18 | 0.63 | 2 | 1 | 1 | 5 | 5 | 5 | 0 | 1 | 0 | 4 | 2 | 3 |
| 19 | 0.16 | 2 | 1 | 1 | 5 | 5 | 5 | 0 | 0 | 0 | 4 | 4 | 3 |
|    | 0.32 | 3 | 2 | 2 | 5 | 5 | 5 | 0 | 1 | 1 | 5 | 5 | 4 |
|    | 0.63 | 4 | 4 | 3 | 5 | 5 | 5 | 1 | 2 | 2 | 5 | 5 | 5 |
| 20 | 0.16 | 1 | 0 | 0 | 4 | 5 | 5 | 0 | 0 | 0 | 4 | 2 | 2 |
|    | 0.32 | 2 | 1 | 1 | 5 | 5 | 5 | 1 | 0 | 1 | 5 | 3 | 3 |
|    | 0.63 | 3 | 2 | 2 | 5 | 5 | 5 | 2 | 1 | 2 | 5 | 4 | 4 |
| 21 | 0.16 | 0 | 0 | 0 | 4 | 5 | 5 | 0 | 0 | 0 | 4 | 3 | 4 |
|    | 0.32 | 1 | 1 | 0 | 5 | 5 | 5 | 1 | 0 | 1 | 5 | 4 | 5 |
|    | 0.63 | 2 | 2 | 1 | 5 | 5 | 5 | 2 | 0 | 2 | 5 | 5 | 5 |
| 22 | 0.63 | 2 | 1 | 1 | 5 | 5 | 5 | 2 | 1 | 2 | 4 | 3 | 3 |

TABLE 3-continued

| Comp. No. | Dose kg/ha | EC | DI | CY | SO | GA | RO | OR | ZE | TR | GL | GO | BE |
|---|---|---|---|---|---|---|---|---|---|---|---|---|---|
| 28 | 1.6 | 3 | 3 | 1 | 5 | 5 | 5 | 1 | 0 | 0 | 4 | 4 | 4 |
|  | 3.2 | 4 | 4 | 2 | 5 | 5 | 5 | 2 | 1 | 1 | 5 | 5 | 5 |
|  | 6.3 | 5 | 5 | 2 | 5 | 5 | 5 | 3 | 2 | 2 | 5 | 5 | 5 |
| Comparative Compound A | 2.5 | 0 | 0 | 0 | 0 | 2 | 0 | 0 | 0 | 0 | 0 | 0 | 0 |
| Comparative Compound B | 2.5 | 0 | 0 | 0 | 0 | 1 | 0 | 0 | 0 | 0 | 0 | 0 | 0 |

Comparative Compounds A and B:
Disclosed in Japanese Unexamined Patent Publication No. 122671/1988.

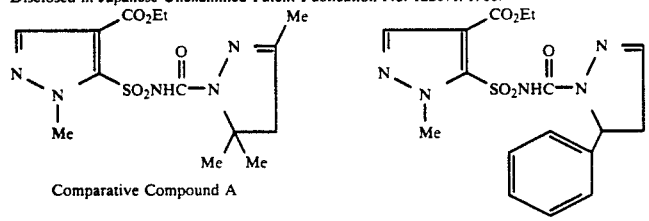

Comparative Compound A

Comparative Compound B

TABLE 4

| No. | g/a | TR | AV | AL |
|---|---|---|---|---|
| 3 | 0.4 | 0 | 4 | 4 |
|  | 0.8 | 0 | 5 | 5 |
|  | 1.6 | 0 | 5 | 5 |
| 19 | 0.4 | 0 | 3 | 3 |
|  | 0.8 | 0 | 4 | 4 |
|  | 1.6 | 0 | 5 | 5 |
| 21 | 0.4 | 0 | 3 | 3 |
|  | 0.8 | 0 | 4 | 4 |
|  | 1.6 | 0 | 5 | 5 |
| Reference* Compound | 0.4 | 0 | 0 | 0 |
|  | 0.8 | 0 | 1 | 1 |
|  | 1.6 | 0 | 2 | 2 |

*Diclofop-methyl

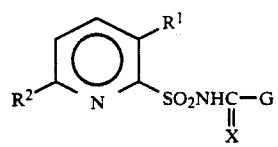

We claim:
1. A pyridinesulfonamide derivative of the formula (I) and a salt thereof:

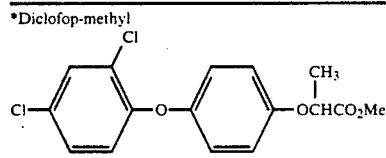

wherein $R^1$ is a halogen atom, a trifluoromethyl group, a $C_1$-$C_6$ alkoxycarbonyl group, a $C_1$-$C_6$ mono- or di-alkylaminocarbonyl group, a $C_1$-$C_6$ alkoxy group, a $C_1$-$C_6$ alkylsulfonyl group, a $C_1$-$C_6$ alkylthio group, a $C_1$-$C_6$ alkyl group substituted by a $C_1$-$C_6$ alkoxy group, a $C_1$-$C_6$ alkyl group substituted by a $C_1$-$C_6$ mono- or poly-halogenoalkoxy group, a $C_1$-$C_6$ mono- or poly-halogenoalkoxy group, a $C_1$-$C_6$ mono- or dialkylaminosulfonyl group, a $C_1$-$C_6$ alkoxyaminosulfonyl group substituted by a $C_1$-$C_6$ alkyl group, a nitro group, a $C_1$-$C_6$ alkyl group substituted by a $C_1$-$C_6$ alkylthio a $C_1$-$C_6$ alkyl group Substituted by a $C_1$-$C_6$ group, a $C_1$-$C_6$ alkyl group substituted by a $C_1$-$C_6$ alkylsulfonyl group, or a $C_1$-$C_6$ alkyl group substituted by a $C_1$-$C_6$ alkoxycarbonyl group;

$R^2$ is a hydrogen atom or a halogen atom;
X is a oxygen atom or a sulfur atom; and

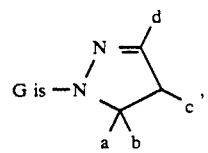

wherein each of a, b, c and d independently represents a hydrogen atom, a $C_1$-$C_6$ alkyl group, a $C_2$-$C_6$ alkenyl group, a $C_2$-$C_6$ alkynyl group, a $C_1$-$C_6$ alkyl group mono- or poly-substituted by a halogen atom, a $C_1$-$C_6$ alkoxy group, a $C_1$-$C_6$ alkyl group substituted by a $C_1$-$C_6$ alkoxy group, a $C_1$-$C_6$ alkoxycarbonyl group, a $C_1$-$C_6$ alkyl group substituted by a $C_1$-$C_6$ alkylthio group, a $C_1$-$C_6$ alkyl group substituted by a $C_1$-$C_6$ alkylsulfonyl group, a $C_1$-$C_6$ alkylthio group, a $C_1$-$C_6$ alkylcarbonyl group, a $C_3$-$C_7$ cycloalkyl group, a $C_3$-$C_7$ cycloalkenyl group, a cyano group, or a phenyl or benzyl group which may be mono- or poly-substituted by a halogen atom, a trifluoromethyl group, a $C_1$-$C_6$ alkyl group, a $C_1$-$C_6$ alkoxy group, a $C_1$-$C_6$ alkoxycarbonyl group or a nitro group.

2. The pyridinesulfonamide derivative of claim 1, which is

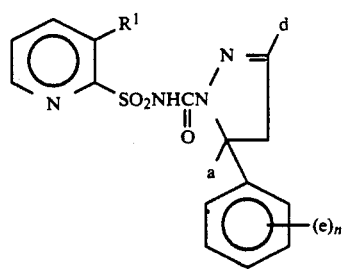

wherein $R^1$ is a halogen group, a trifluoromethyl group or a dimethylaminocarbonyl group;
a is a hydrogen atom or a methyl group;
d is a hydrogen atom or a $C_1$-$C_3$ alkyl group;
e is a hydrogen atom, a halogen atom, a trifluoromethyl group or a methoxy group;
n is 1 or 2.

3. The pyridinesulfonamide derivative of claim 1, which is

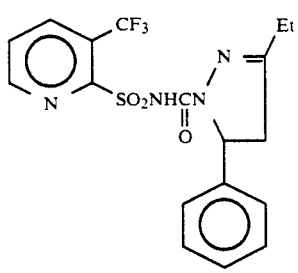

4. The pyridinesulfonamide derivative of claim 1, which is

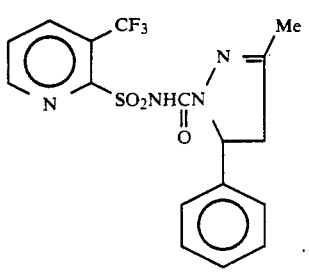

5. The pyridinesulfonamide derivative of claim 1, which is

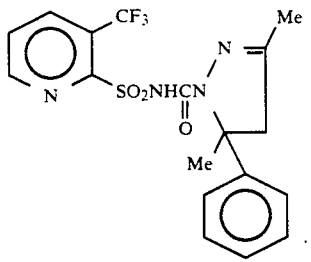

6. The pyridinesulfonamide derivative of claim 1, which is

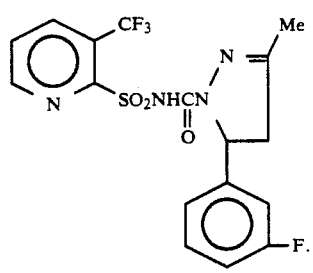

7. The pyridinesulfonamide derivative of claim 1, which is

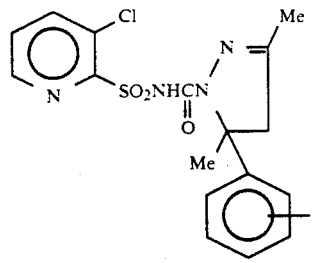

8. The pyridinesulfonamide derivative of claim 1, which is

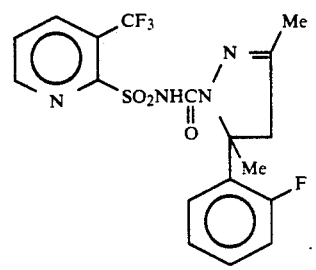

9. A selective herbicide containing an effective amount of the compound of claim 1 as an active ingredient, in admixture with a carrier.

10. The selected herbicide of claim 9, wherein the compound is

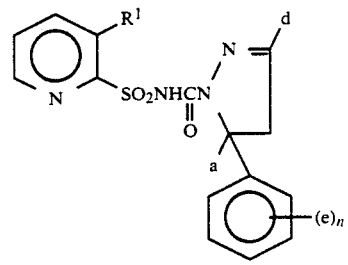

wherein $R^1$ is a halogen group, a trifluoromethyl group or a dimethylaminocarbonyl group;
  a is a hydrogen atom or a methyl group;
  d is a hydrogen atom or a $C_1-C_3$ alkyl group;
  e is a hydrogen atom, a halogen atom, a trifluoromethyl group or a methoxy group;
  n is 1 or 2.

11. The selective herbicide of claim 9, wherein the compound is

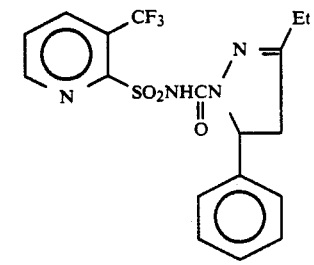

12. The selective herbicide of claim 9, wherein the compound is

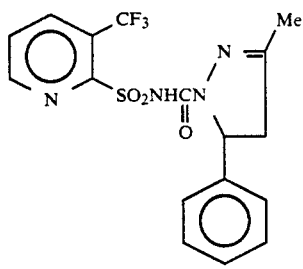

13. The selective herbicide of claim 9, wherein the compound is

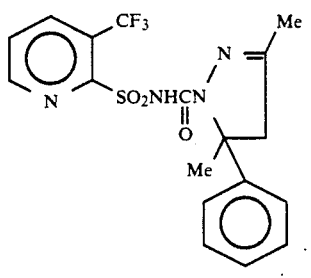

14. The selective herbicide of claim 9, wherein the compound is

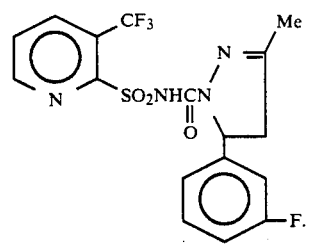

15. The selective herbicide of claim 9, wherein the compound is

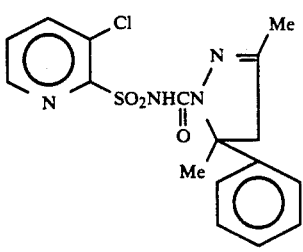

16. The selective herbicide of claim 9, wherein the compound is

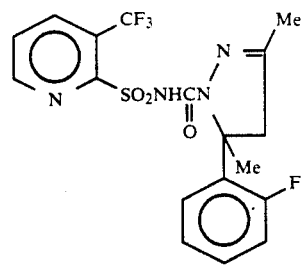

17. A method of treating crop plants which comprises administering a herbicidally effective amount of the compound of claim 1 as an active ingredient.

18. The method of claim 17, wherein the compound is

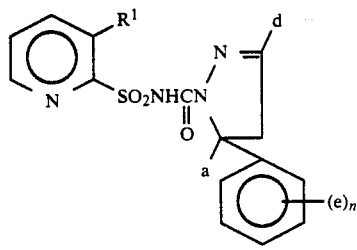

wherein $R^1$ is a halogen group, a trifluoromethyl group or a dimethylaminocarbonyl group;
  a is a hydrogen atom or a methyl group;
  d is a hydrogen atom or a $C_1$-$C_3$ alkyl group;
  e is a hydrogen atom, a halogen atom, a trifluoromethyl group or a methoxy group;
  n is 1 or 2.

19. The method of claim 17, wherein the compound is

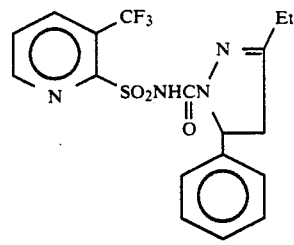

20. The method of claim 17, wherein the compound is

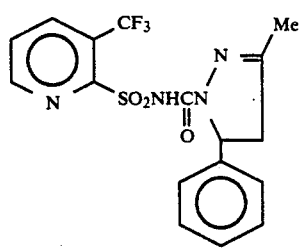

21. The method of claim 17, wherein the compound is

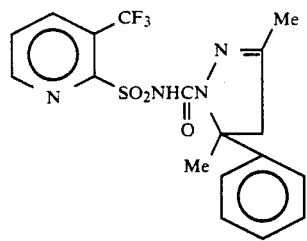
22. The method of claim 17, wherein the compound is
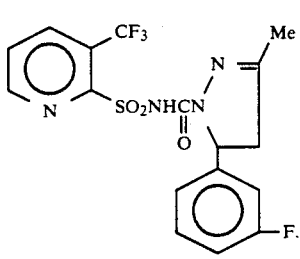
23. The method of claim 17, wherein the compound is
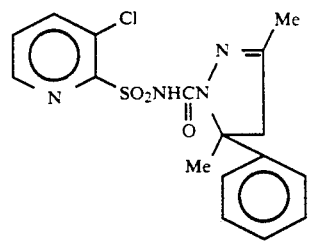
24. The method of claim 17, wherein the compound is
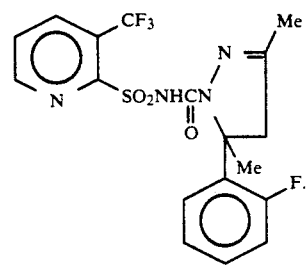
* * * * *

UNITED STATES PATENT AND TRADEMARK OFFICE
CERTIFICATE OF CORRECTION

PATENT NO. : 5,116,405
DATED : May 26, 1992
INVENTOR(S) : Kenzi MAKINO, et al.

It is certified that error appears in the above-identified patent and that said Letters Patent is hereby corrected as shown below:

Line 15 of the abstract, "$C_1-C_5$" should read, --$C_1-C_6$--.

Line 19 of the abstract, "a sulfur atoms;" should read --a sulfur atom;--.

Column 2, line 23, "Substituted" should read --substituted--.

Column 2, line 40, "a $C_1$-group," should read --a $C_1-C_6$ alkoxy group,--.

Column 2, line 44, "Substituted" should read --substituted--.

Column 2, line 67, insert --be-- after "may".

Column 5, line 37, delete ")" (first occurrence), and insert --(--.

Column 38, formula G262,

UNITED STATES PATENT AND TRADEMARK OFFICE
CERTIFICATE OF CORRECTION

PATENT NO. : 5,116,405
DATED : May 26, 1992
INVENTOR(S) : Kenzi MAKINO, et al.

It is certified that error appears in the above-identified patent and that said Letters Patent is hereby corrected as shown below:

Column 49, formula G366,

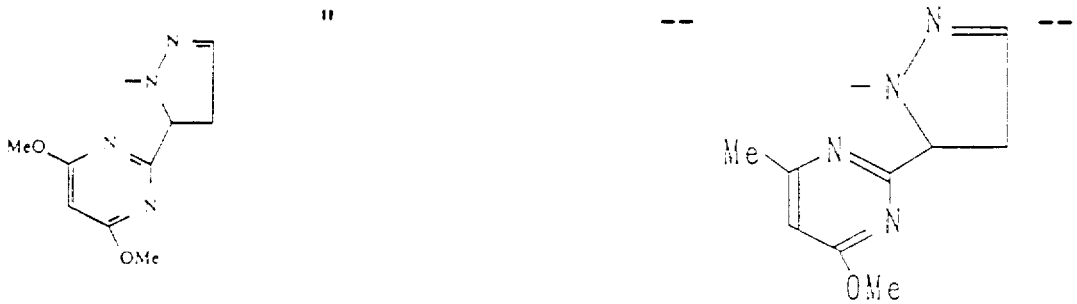

should be shown as

Column 62, line 32, "0.0005" should read --0.005--.

Column 63, line 37, "edscendens" should read --adscendens--.

Column 67, line 63, insert --group,-- after "alkylthio", "Substituted" should read --substituted--.

Column 67, delete line 64 entirely.

UNITED STATES PATENT AND TRADEMARK OFFICE
CERTIFICATE OF CORRECTION

PATENT NO. : 5,116,405
DATED : May 26, 1992
INVENTOR(S) : Kenzi MAKINO, et al.

It is certified that error appears in the above-identified patent and that said Letters Patent is hereby corrected as shown below:

Column 70, claim 7, formula

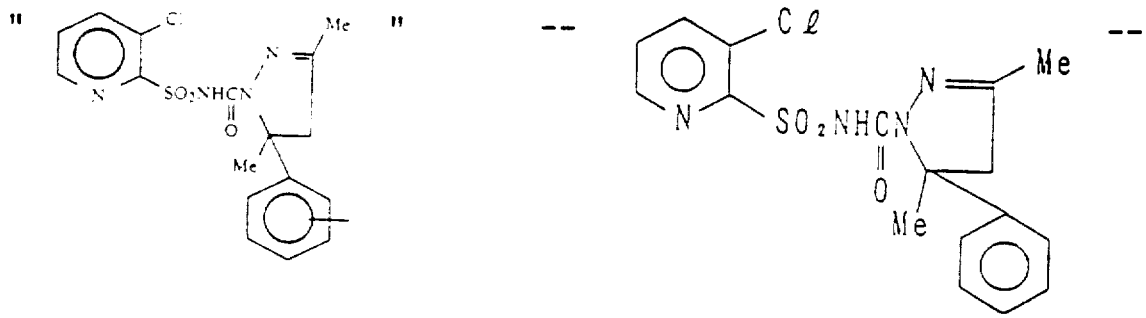

should be shown as  .

Signed and Sealed this

First Day of February, 1994

Attest:

BRUCE LEHMAN

Attesting Officer          Commissioner of Patents and Trademarks